US012575824B2

(12) United States Patent
Osawa et al.

(10) Patent No.: US 12,575,824 B2
(45) Date of Patent: Mar. 17, 2026

(54) KNOT TYING DEVICE

(71) Applicant: Brother Kogyo Kabushiki Kaisha, Nagoya (JP)

(72) Inventors: Naokatsu Osawa, Nagoya (JP); Junji Yamano, Kariya (JP); Ryuta Iijima, Nagoya (JP); Masashi Ichihashi, Mizuho (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 39 days.

(21) Appl. No.: 18/673,676

(22) Filed: May 24, 2024

(65) Prior Publication Data

US 2024/0325017 A1     Oct. 3, 2024

Related U.S. Application Data

(63) Continuation of application No. PCT/JP2022/043550, filed on Nov. 25, 2022.

(30) Foreign Application Priority Data

Nov. 26, 2021    (JP) ................................. 2021-192561

(51) Int. Cl.
*A61B 17/04*          (2006.01)
(52) U.S. Cl.
CPC .... *A61B 17/0469* (2013.01); *A61B 2017/047* (2013.01); *A61B 2017/0474* (2013.01)
(58) Field of Classification Search
CPC .......... A61B 17/0469; A61B 2017/047; A61B 2017/0474
See application file for complete search history.

(56) References Cited

U.S. PATENT DOCUMENTS

| | | | |
|---|---|---|---|
| 5,437,682 A | 8/1995 | Grice et al. | |
| 5,702,407 A | 12/1997 | Kaji | |

(Continued)

FOREIGN PATENT DOCUMENTS

| | | |
|---|---|---|
| JP | H06-054855 A | 3/1994 |
| JP | 2018-029678 A | 3/2018 |
| WO | 2019-211954 A1 | 11/2019 |

OTHER PUBLICATIONS

Feb. 7, 2023—International Search Report—Intl App PCT/JP2022/043550.

(Continued)

*Primary Examiner* — Phong Son H Dang
(74) *Attorney, Agent, or Firm* — Banner & Witcoff, Ltd.

(57)          ABSTRACT

A knot tying device includes a holding portion, a first loop forming portion, a positioning portion, and a first suture hook. The holding portion including a suture hooking portion at its distal end portion. The holding portion is configured to hold a suture that is engaged with the suture hooking portion. The first loop forming portion is configured to form a loop of the suture fixedly. The positioning portion is configured to position the suture hooking portion with which the suture is engaged, at a specific position. The first suture hook is configured to pass through the loop, and catch and hold the suture in a state where the suture hooking portion with which the suture is engaged is located at the specific position. The first suture hook causes the suture to pass through the loop, thereby tying a knot in the suture.

15 Claims, 48 Drawing Sheets

(56) References Cited

U.S. PATENT DOCUMENTS

| | | | | |
|---|---|---|---|---|
| 5,749,898 A | * | 5/1998 | Schulze ............. | A61B 17/0469 |
| | | | | 606/228 |
| 2011/0046643 A1 | | 2/2011 | Milad et al. | |
| 2019/0231346 A1 | | 8/2019 | Sakano et al. | |
| 2021/0045733 A1 | | 2/2021 | Osawa et al. | |
| 2022/0110627 A1 | * | 4/2022 | Tu ...................... | A61B 17/0469 |
| 2024/0341750 A1 | * | 10/2024 | Brady ................ | A61B 17/0469 |

OTHER PUBLICATIONS

May 2, 2024—(WO) International Preliminary Report on Patentability and Written Opinion—Intl App PCT/JP2022/043550, Eng Tran.

* cited by examiner

KNOT TYING DEVICE

REFERENCE TO RELATED APPLICATIONS

This is a continuation application of International Application No. PCT/JP2022/043550 filed on Nov. 25, 2022, which claims priority from Japanese Patent Application No. 2021-192561 filed on Nov. 26, 2021. The entire contents of the aforementioned applications are incorporated herein by reference.

BACKGROUND ART

A known suturing device is configured to suture an entire suture portion of a to-be-sutured object using a suture instead of using metal staples in suturing of the to-be-sutured object in, for example, a field of living body surgery.

Such a known suturing device includes a needle and a shuttle. The needle holds a first suture and is reciprocable in a certain direction. The shuttle includes a holding portion, a first hook-shaped end portion and a second hook-shaped end portion. The holding portion holds a second suture. The first hook-shaped end portion and the second hook-shaped end portion are disposed at respective end portions of the shuttle with respect to an axis extending in a direction in which the needle reciprocates. The shuttle is rotatable in both directions about the axis extending in the direction in which the needle reciprocates.

According to such a suturing device, the shuttle includes the first hook-shaped end portion and the second hook-shaped end portion at opposite sides of the holding portion, respectively, and is rotatable in both the directions about the axis extending in the direction in which the needle reciprocates. Thus, the holding portion is caused to pass through a loop of the first suture from each side by turns, thereby causing a second suture held by the holding portion and the first suture to pass through each other relatively in respective directions. Thus, such a mechanical action in response to a simple operation enables to a stitch or a knot to be formed readily and reliably.

SUMMARY

In the known suturing device, in response to the needle that has penetrated a living tissue moving backward by a certain amount, the first suture extending from a distal end portion of the needle may be separated from the distal end portion of the needle, and thus a semi-annular loop may be formed. The shuttle holding the second suture may be caused to pass through the loop formed by the first suture, thereby forming a stitch or knot.

The shape of the loop formed by the first suture may be maintained by its own rigidity. Thus, if, however, the loop is affected by, for example, a surface tension of body fluids of a living body or a weight of the attached body fluids, the loop may be difficult to maintain its shape. This may become obstacle to a reliable formation of a stitch or knot.

Accordingly, aspects of the disclosure provide a knot tying device capable of stably forming a loop in a suture in knot tying.

In one or more aspects of the disclosure, a knot tying device may include: a holding portion including a suture hooking portion at its distal end portion, the holding portion configured to hold a suture that is engaged with the suture hooking portion; a first loop forming portion configured to form a loop of the suture fixedly; a positioning portion configured to position the suture hooking portion with which the suture is engaged, at a specific position; a first suture hook configured to pass through the loop and catch and hold the suture in a state where the suture hooking portion with which the suture is engaged is located at the specific position, wherein the first suture hook causes the suture to pass through the loop, thereby tying a knot in the suture.

According to the knot tying device of the one or more aspects of the disclosure, in a state where a first loop is fixedly formed by the loop forming portion, the first suture hook may move through the loop, and may catch and hold the suture in a state where the suture hooking portion on which the suture is hooked is located at the specific position, whereby a knot may be tied in the suture. Thus, a loop of the suture may be fixedly formed by the loop forming portion. Consequently, the loop may be stably formed without being affected by, for example, a surface tension of body fluids, a weight of attached body fluids, or other matters. The stable loop formation enables stable knot tying in the suture.

DESCRIPTION

Hereinafter, an illustrative embodiment of the disclosure will be described in detail with reference to the drawings.

First Illustrative Embodiment

Figure 1:
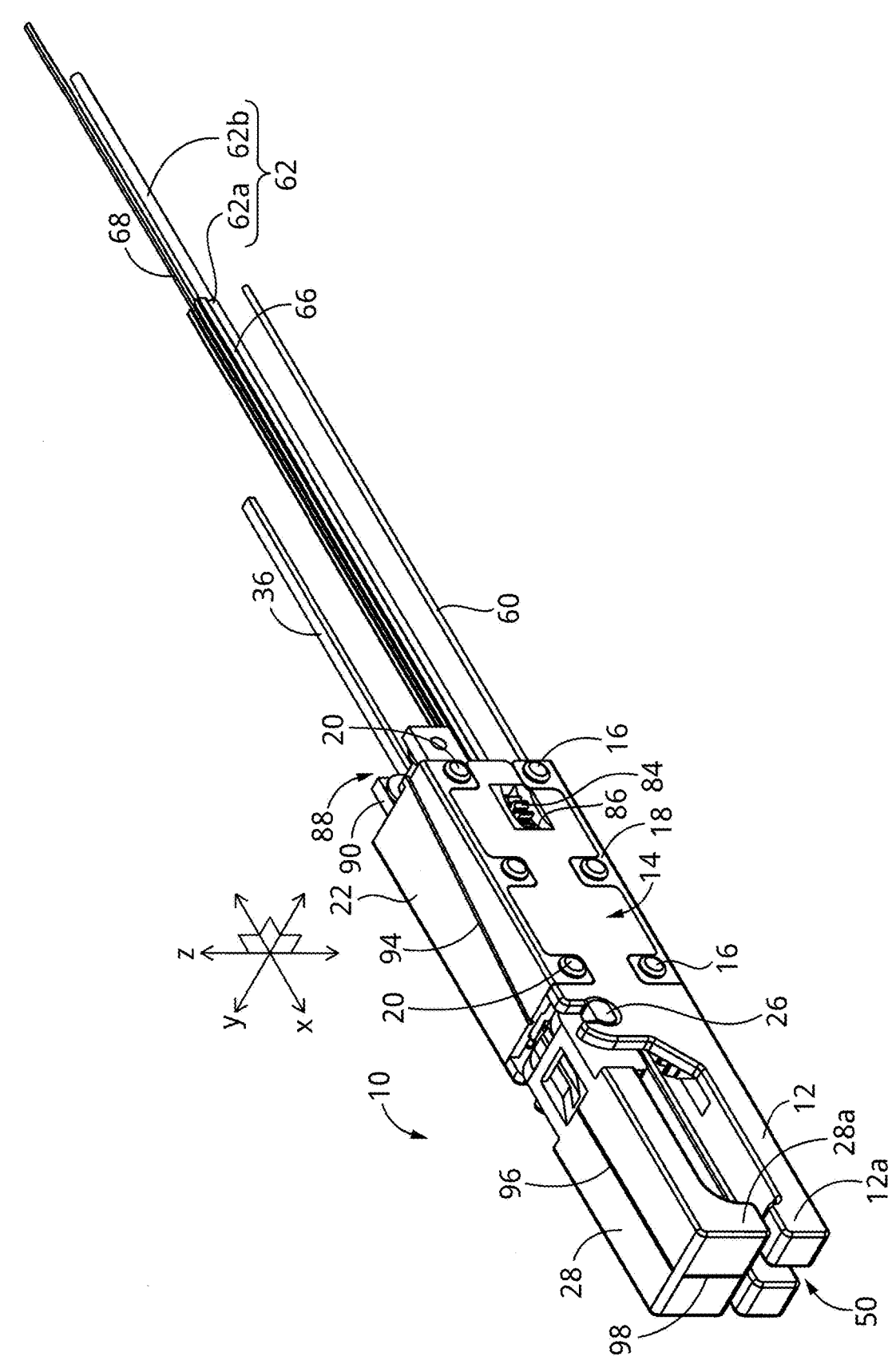
FIG. 1 is a perspective view of a knot tying device according to an illustrative embodiment of the disclosure as viewed obliquely from above.
Figure 2:
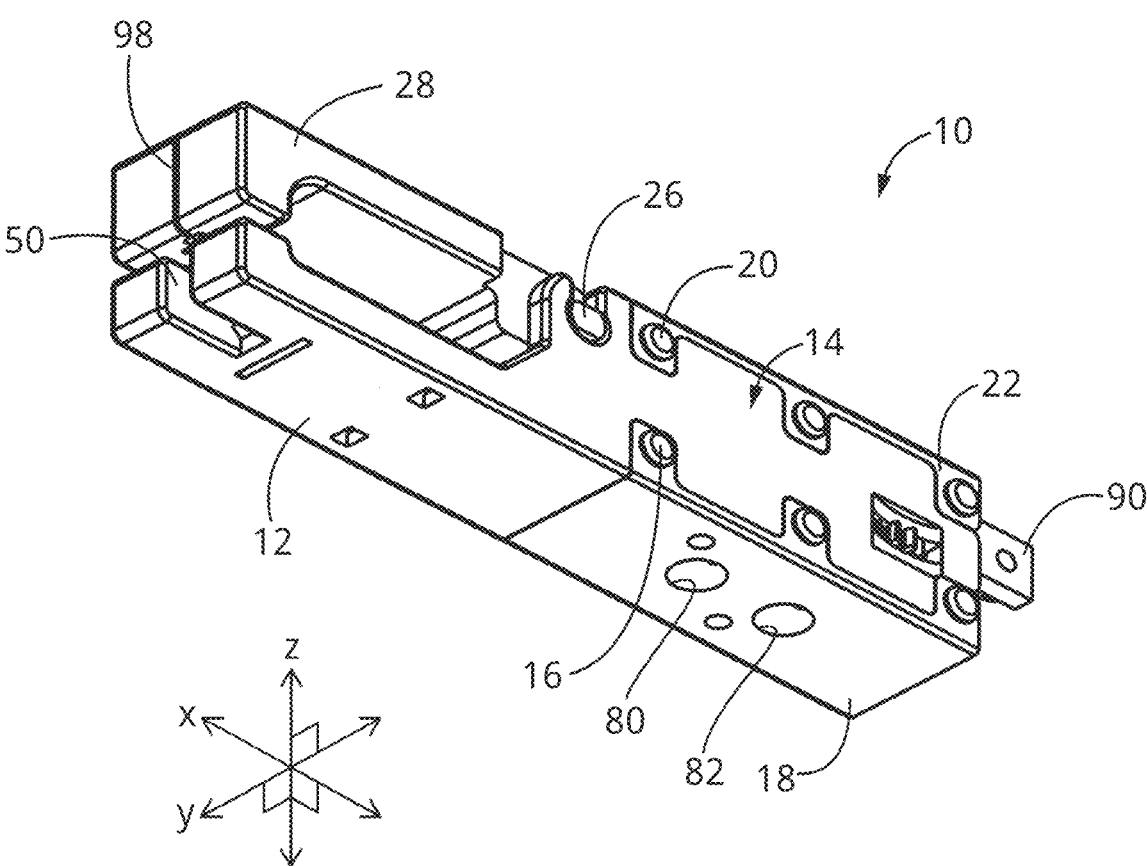
FIG. 2 is a perspective view of the knot tying device of FIG. 1 as viewed obliquely from below.

As illustrated in FIGS. 1 to 9, a knot tying device 10 according to an illustrative embodiment of the disclosure has a longitudinal shape as a whole, and is configured to open and close its distal end portion to hold a to-be-tied object 30 (refer to FIG. 26 and other applicable drawings) and form a knot and a stitch on the to-be-tied object 30. The knot tying device 10 also serves as a suturing device for the to-be-tied object 30. In the illustrative embodiment, as illustrated in FIG. 1, a direction perpendicular to a longitudinal direction x of the knot tying device 10 and parallel to a separable surface of the distal end portion is defined as a height direction z, and a direction perpendicular to the longitudinal direction x and the height direction z is defined as a width direction y.

The knot tying device 10 includes a main body 14, a first lid member 18, a second lid member 22, and a second jaw portion 28. The main body 14 includes a first jaw portion 12 at a lower side of the distal end portion. The first lid member 18 is fixed to the main body 14 using six first fastening screws 16 at both side surfaces of a proximal-end-side portion of the main body 14 to cover a lower surface of the main body 14. The second lid member 22 is fixed to the main body 14 using six second fastening screws 20 at both side surfaces of the proximal-end-side portion of the main body 14 to cover an upper surface of the main body 14. The upper surface is another surface of the proximal-end-side portion of the main body 14. The second jaw portion 28 includes a rotary shaft 26 removably received in a concave bearing surface 24 defined at a middle portion of the main body 14 in the longitudinal direction x. The second jaw portion 28 is rotatable about the rotary shaft 26 with respect to the first jaw portion 12 so as to move toward and away from the first jaw portion 12.

Figure 3:
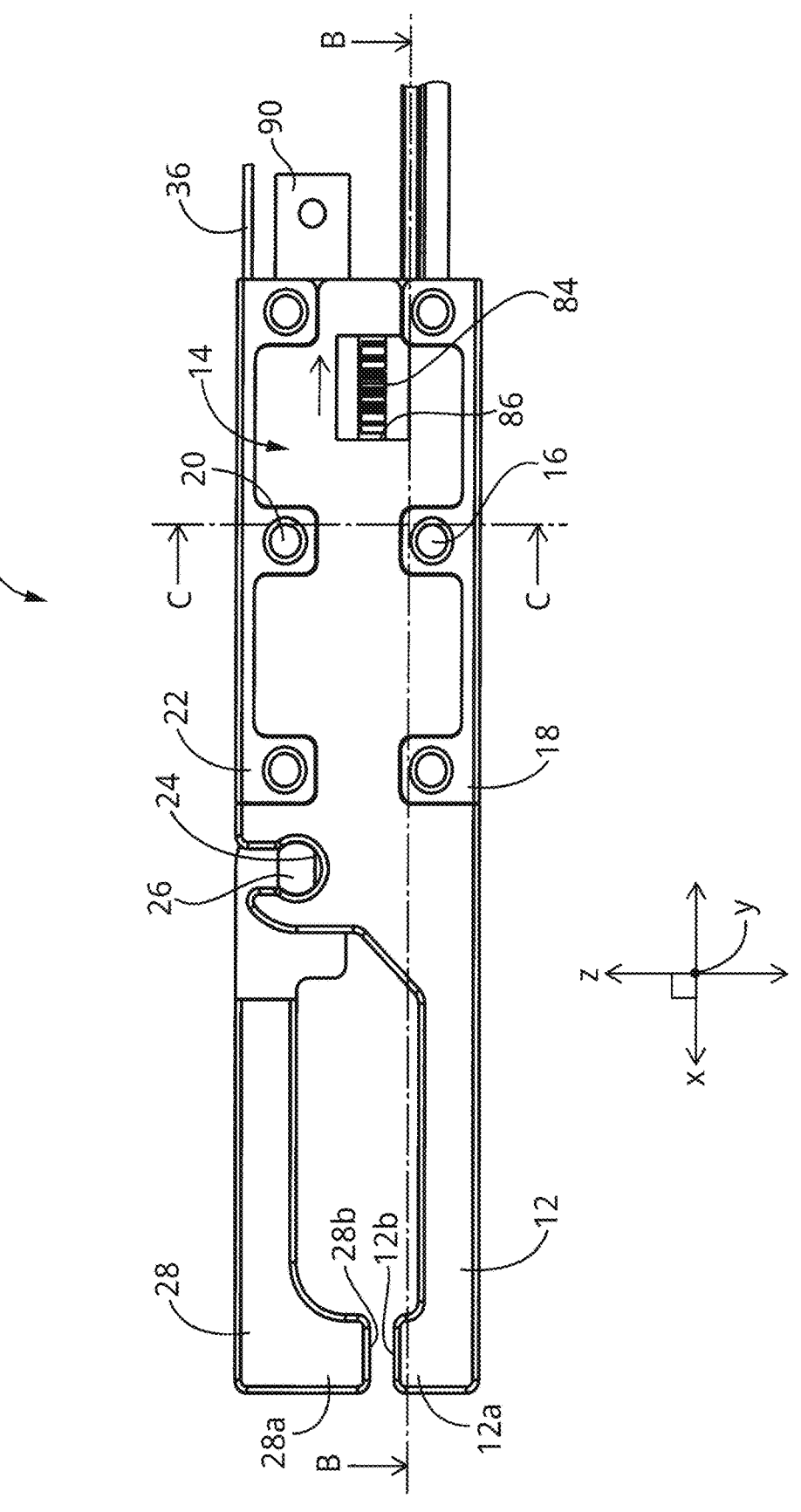
FIG. 3 is a front view of the knot tying device of FIG. 1.
Figure 10:
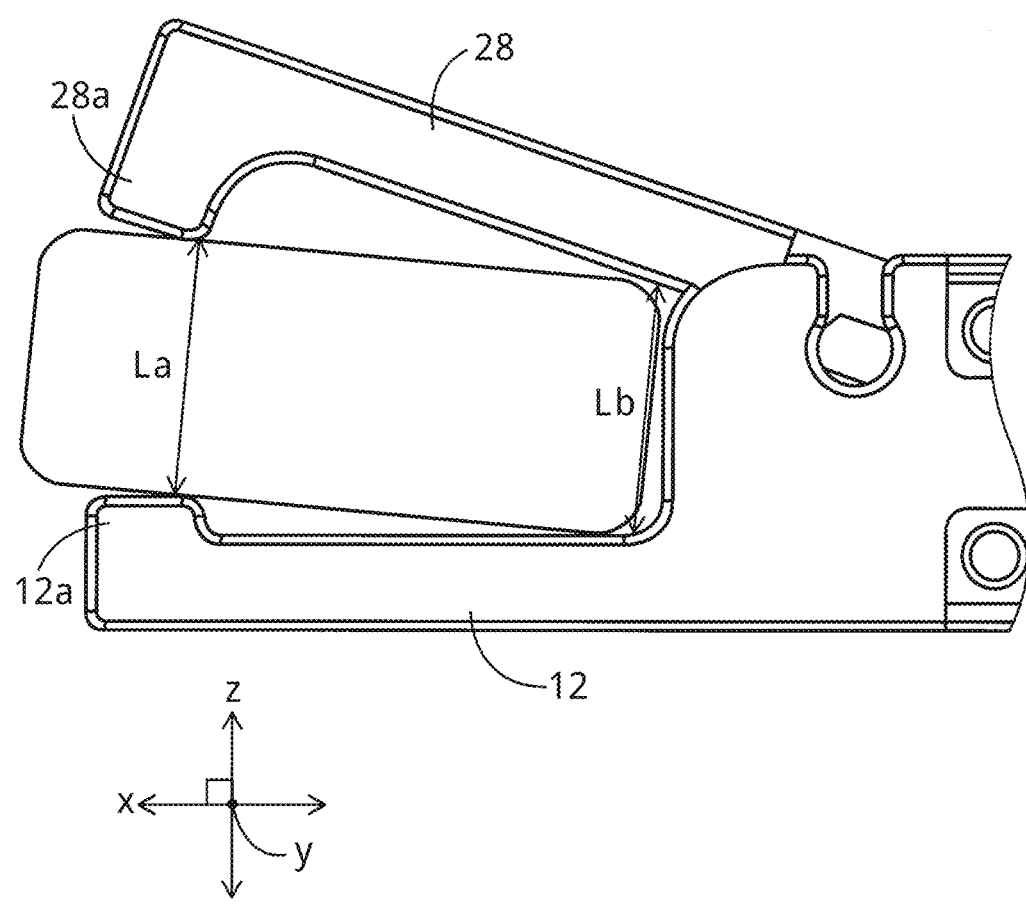
FIG. 10 is an enlarged view of the knot tying device of FIG. 1 whose distal end portion is opened.

As illustrated in detail in FIG. 3, the first jaw portion 12 includes a first holding protrusion 12a at its distal end, and the second jaw portion 28 includes a second holding protrusion 28a at its distal end. The first holding protrusion 12a and the second holding protrusion 28a protrude toward each other in the height direction z. The first holding protrusion 12a has a first holding surface 12b. The second holding protrusion 28a has a second holding surface 28b. The first holding surface 12b and the second holding surface 28b face each other. In a state where the first jaw portion 12 and the second jaw portion 28 are closed, the first holding surface 12b of the first holding protrusion 12a and the second holding surface 28b of the second holding protrusion 28a are adjacent to each other. In this state, a space is left between a particular portion of the first jaw portion 12 and a particular portion of the second jaw portion 28 so that the first jaw portion 12 and the second jaw portion 28 are free from contacting the to-be-tied object 30. The particular portion of the first jaw portion 12 is a portion other than the first holding protrusion 12a in the first jaw portion 12. The particular portion of the second jaw portion 28 is a portion other than the second holding protrusion 28a in the second jaw portion 28. In knot tying, a to-be-tied object that is at least a portion of a living body such as a living tissue or a vessel, that is, a to-be-tied object 30 is held by the first holding surface 12b and the second holding surface 28b. FIG. 10 illustrates a state where the second jaw portion 28 is moved away from the first jaw portion 12 to a maximum angle at which suturing or knot tying can be performed. A (minimum) distance La between the first holding protrusion 12a and the second holding protrusion 28a is less than a distance Lb between the a proximal end portion of the first jaw portion 12 and a proximal end portion of the second jaw portion 28 (La≤Lb).

Figure 7:
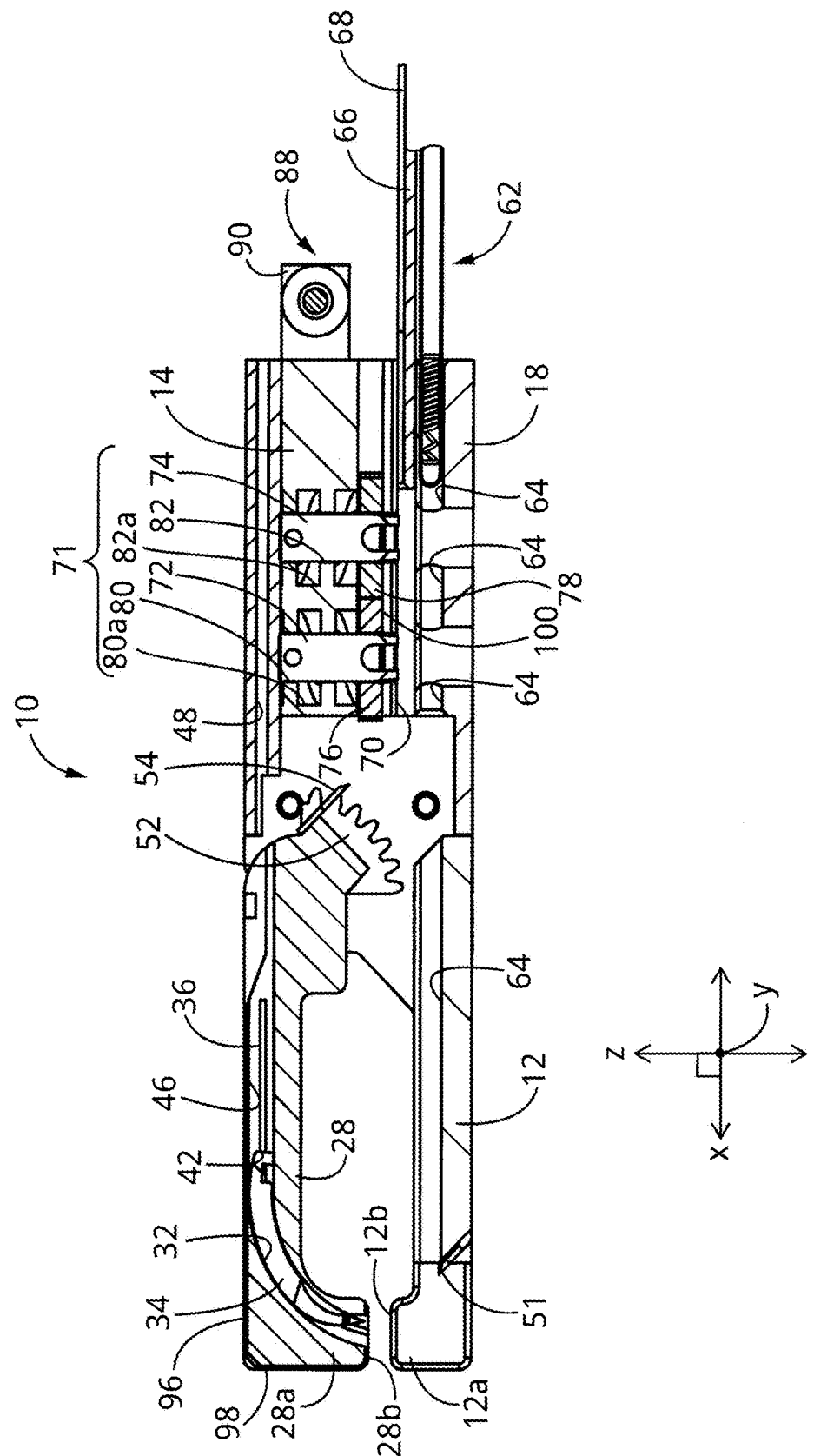
FIG. 7 is a sectional view taken along line A-A of FIG. 4.

As illustrated in detail in FIG. 7, the second jaw portion 28 has an arc-shaped needle housing hollow 32 in its distal end portion. The needle housing hollow 32 is open at a central portion of the second holding surface 28b. An arc-shaped curved needle 34 that functions as a suture needle is movably housed in the needle housing hollow 32. The curved needle 34 corresponds to a holding portion that holds a suture L (refer to FIGS. 8 and 26) that is threaded into a needle hole 38 (refer to FIG. 11) that functions as a suture hooking portion.

Figure 11:
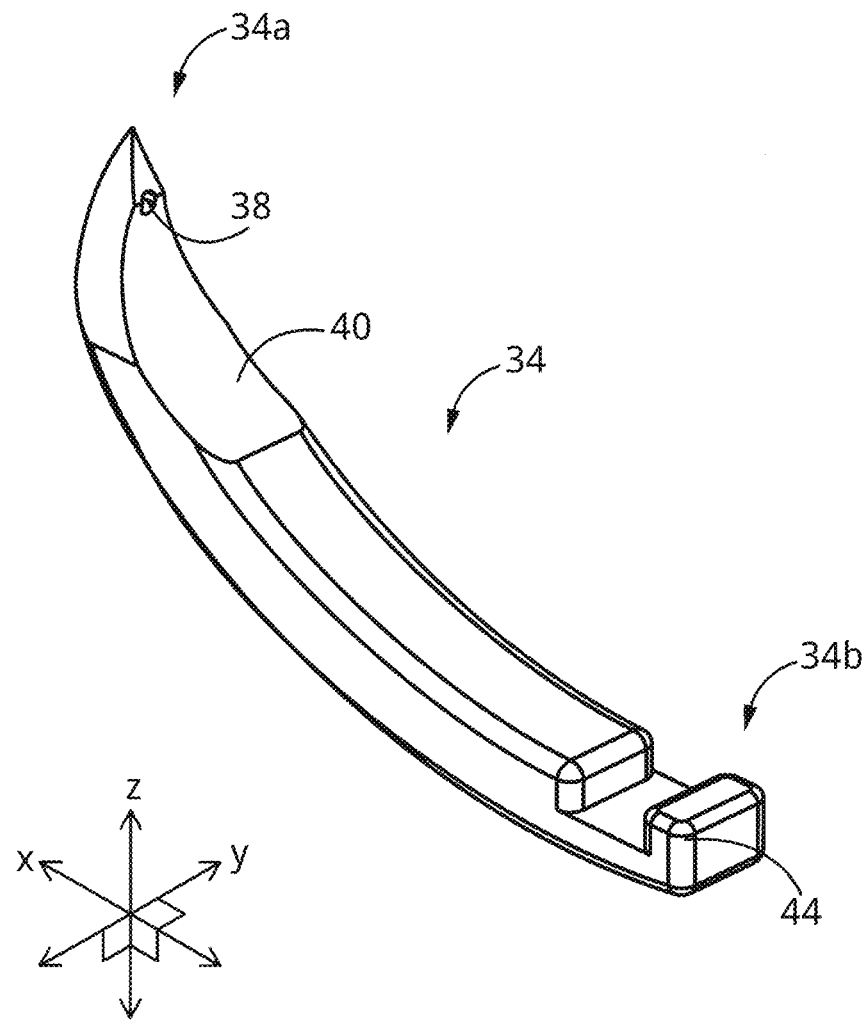
FIG. 11 is a perspective view of a curved needle used in the knot tying device of FIG. 1.

As illustrated in FIG. 11, for example, the curved needle 34 has a sharp pointed tip portion 34a and a base end portion 34b. The base end portion 34b is connected to a needle operating member 36 of FIG. 7 to be used for operating the curved needle 34. The pointed tip portion 34a has the needle hole 38 and a recessed portion 40. The needle hole 38 functions as the suture hooking portion. The recessed portion 40 is defined adjacent to the needle hole 38 and at an inner surface of the curved needle 34 in order to avoid interference with a first suture hook 62 for holding the suture L extending between the curved needle 34 and the to-be-tied object 30. The base end portion 34b includes an engagement projection 44 that engages with an engagement hole 42 (refer to FIG. 7) that needle operating member 36 has at its distal end portion.

As illustrated in detail in FIG. 7, the needle operating member 36 is a flexible member made of, for example, a cut plate spring material having a tape shape and a constant width. The needle operating member 36 protrudes rearward from a rear end of the knot tying device 10 through a needle operating member guide hole 46 of the second jaw portion 28 and a needle operating member guide hole 48 of the second lid member 22. The needle operating member 36 corresponds to a positioning portion that causes the suture hooking portion (e.g., the needle hole 38) on which the suture L is hooked to be located at a specific position such that the curved needle 34 penetrates the to-be-tied object 30 by insertion.

Figure 5:
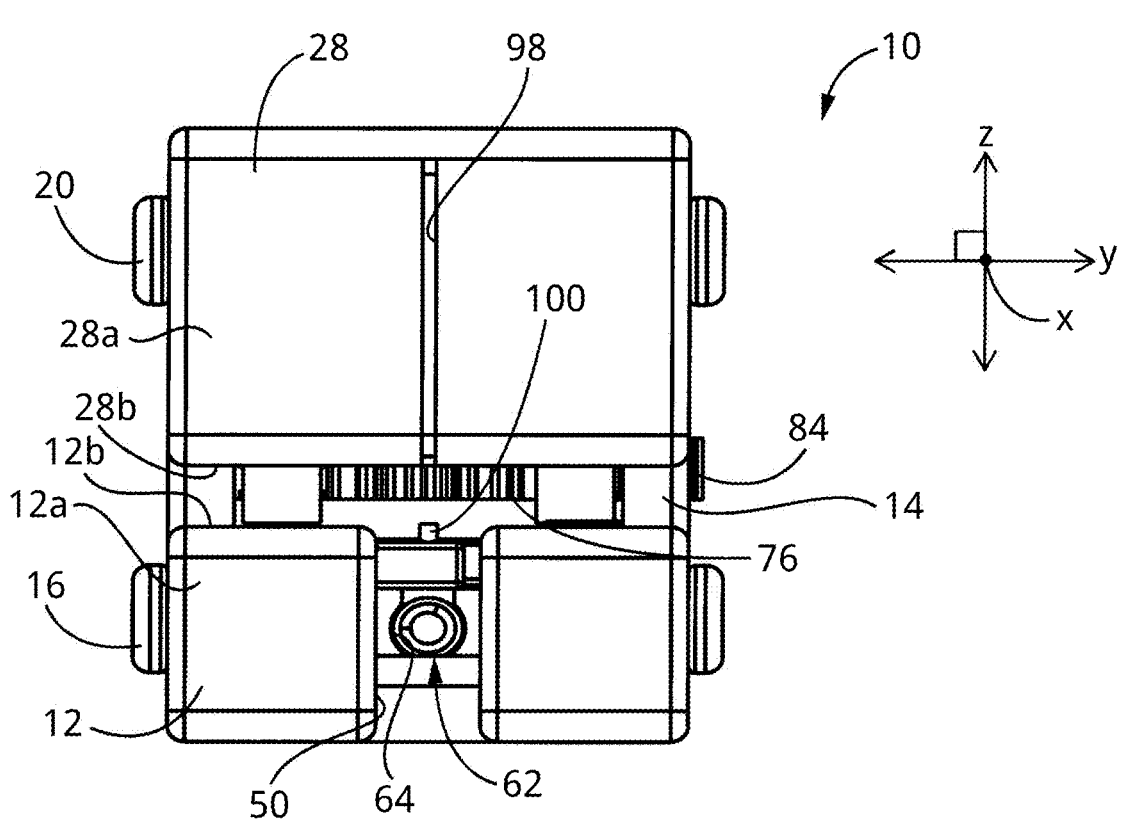
FIG. 5 illustrates the knot tying device of FIG. 1 as viewed from its distal end.
Figure 28:
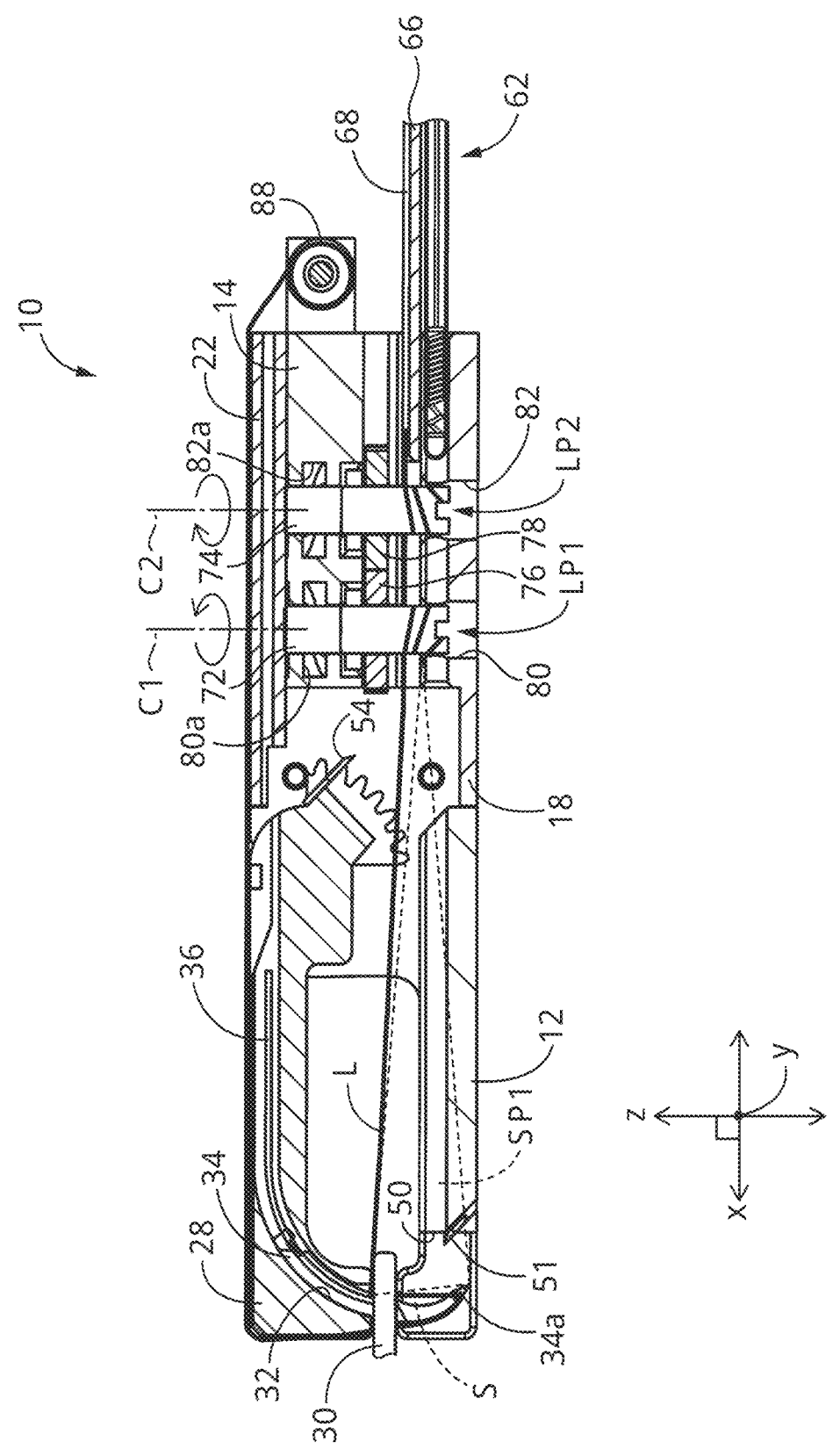
FIG. 28 illustrates a loop forming step in which the first suture loop shaft and the second suture loop shaft rotate to fixedly form a first suture loop and a second suture loop in the knot tying device of FIG. 1, and a needle penetrating step in which the curved needle penetrates the to-be-tied object in the knot tying device of FIG. 1.

As illustrated in detail in FIGS. 1, 5, and 7, the first jaw portion 12 has a slot 50 in a middle portion of the first jaw portion 12 in the width direction y and the slot 50 extends along the longitudinal direction x from the distal end of the first jaw portion 12. In response to the needle operating member 36 being pushed toward the distal end of the knot tying device 10 in a state where the second jaw portion 28 is closed, as illustrated in FIG. 28, the pointed tip portion 34a of the curved needle 34 protrudes relative to the second holding surface 28b (refer to FIG. 7) having the opening of the needle housing hollow 32, and reaches the slot 50 of the first jaw portion 12. In response to the needle operating member 36 being pulled toward the outside from the proximal end portion of the knot tying device 10 along the longitudinal direction x, the curved needle 34 is housed in the needle housing hollow 32. A first cutter 51 is disposed in the first jaw portion 12. In response to the curved needle 34 protruding by a maximum amount relative to the second holding surface 28b (refer to FIG. 7) of the second jaw portion 28 in a state where the second jaw portion 28 is closed, the first cutter 51 cuts the suture L that has passed through the to-be-tied object 30 together with the needle hole 38 (refer to FIG. 11) of the curved needle 34 and has been pulled by the first suture hook 62.

Figure 8:
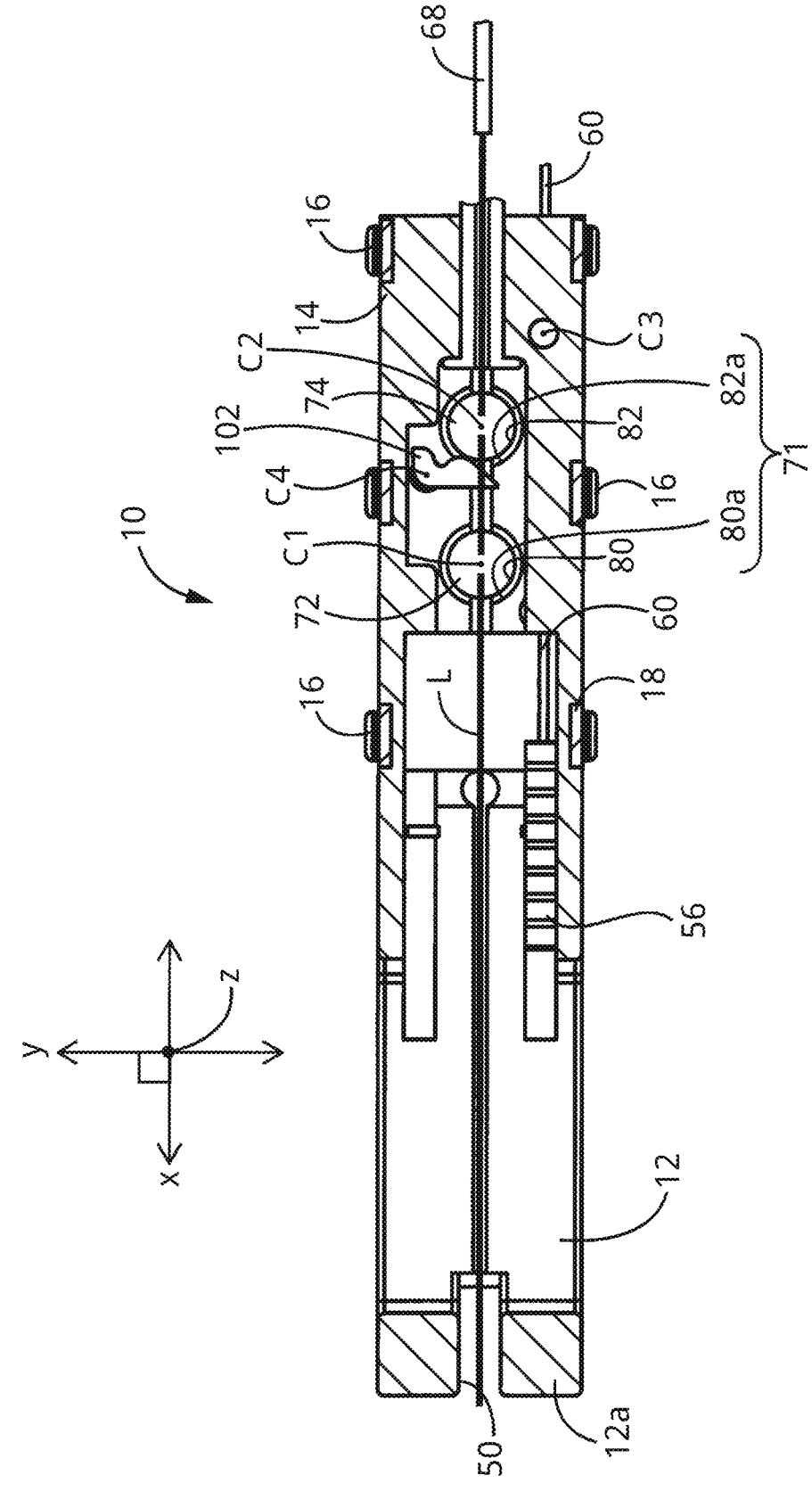
FIG. 8 is a sectional view taken along line B-B of FIG. 3.
Figure 26:
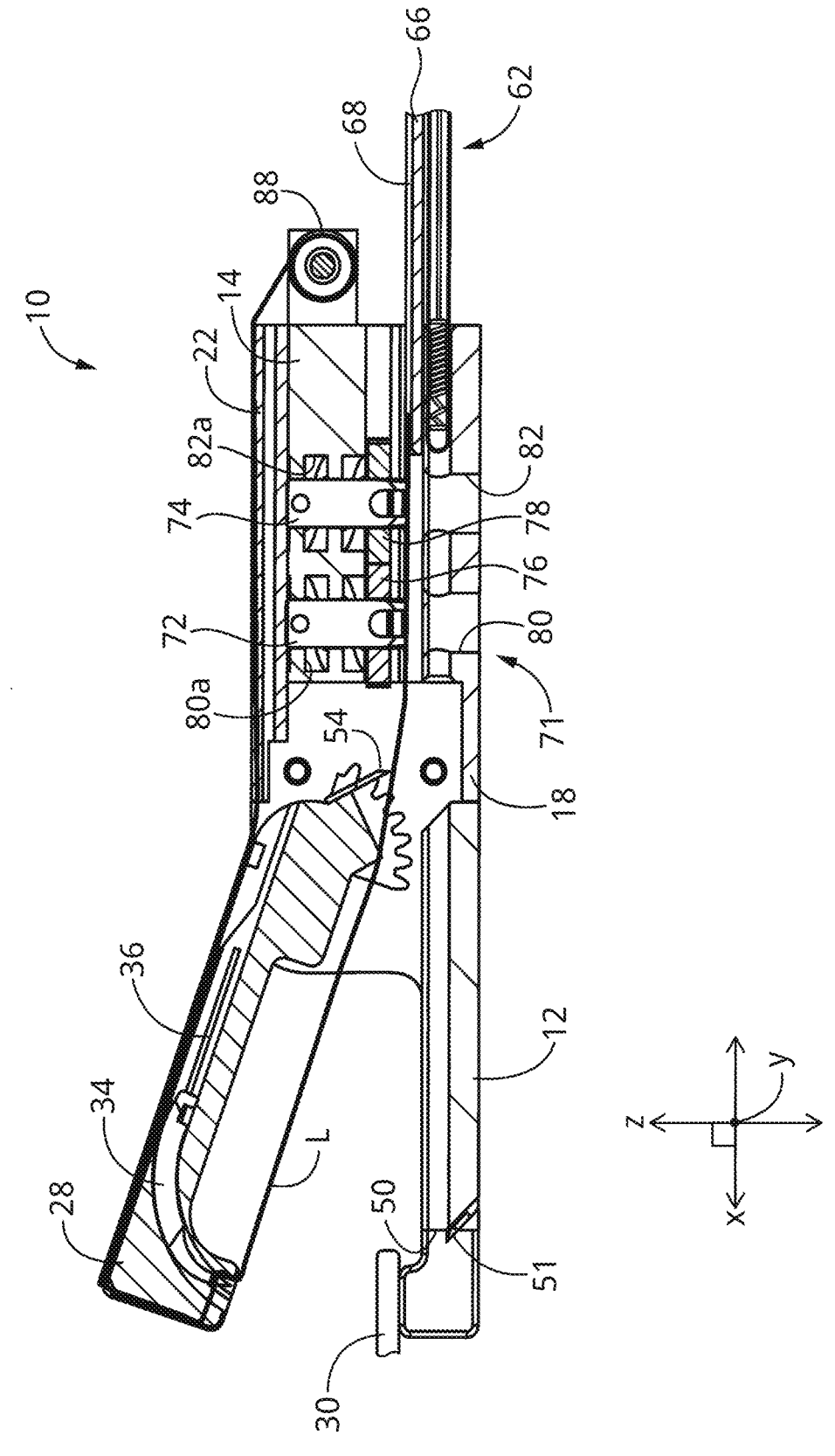
FIG. 26 illustrates the knot tying device of FIG. 1 whose distal end portion is opened.

As illustrated in detail in FIG. 7, a sector member 52 and a second cutter 54 are fixed to the proximal end portion of the second jaw portion 28. The sector member 52 is a sector gear. As illustrated in FIG. 8, a rack 56 that meshes with the sector member 52 is disposed in the main body 14 so as to be movable in the longitudinal direction x of the main body 14. The rack 56 is connected to an opening/closing operation rod 60. The first lid member 18 has an opening/closing rod guide hole 58 extending in the longitudinal direction x. The opening/closing operation rod 60 is guided by the opening/closing operation rod guide hole 58. In response to the opening/closing operation rod 60 being moved forward with respect to the main body 14, the second jaw portion 28 is opened as illustrated in FIG. 26. In response to the opening/closing operation rod 60 being moved backward with respect to the main body 14, the second jaw portion 28 is closed as illustrated in FIGS. 1 to 6.

The opening/closing operation rod 60 preferably includes a cylindrical member and a wire. The cylindrical member is abutted against a rear end surface of the rack 56. The wire is connected to the rear end surface of the rack 56 of FIG. 8 and extends through the cylindrical member. In this case, the cylindrical member is used for moving the rack 56 toward the distal end of the knot tying device 10, and the wire is used for moving the rack 56 toward the proximal end of the knot tying device 10.

As illustrated in detail in FIG. 7, the first lid member 18 has a first guide hole 64 for guiding the first suture hook 62. The first guide hole 64 extends in parallel to the longitudinal direction x of the main body 14. A second guide hole 70 for guiding a knot pusher 66 and a second suture hook 68 is defined in a surface, facing the first lid member 18, of the main body 14. The second guide hole 70 extends in parallel with the longitudinal direction x. While the first suture hook 62 is in a loosely-holding state, the first suture hook 62 is moved in a direction away from the to-be-tied object 30. In the loosely-holding state, the first suture hook 62 has passed through a first suture loop LP1 and a second suture loop LP2 by its movement toward the distal end and loosely holds the suture passing through the to-be-tied object 30 together with the curved needle 34. The first suture hook 62 is further moved backward in the loosely-holding state where the first suture hook 62 loosely holds the suture, after the suture L is cut at a particular point between the curved needle 34 and the first suture hook 62, thereby passing through the pair of first suture loop LP1 and second suture loop LP2. Thereafter, the first suture hook 62 is held on standby in a securely-holding state where the first suture hook 62 securely holds the suture L, and shifts a location of the first suture loop LP1 toward the to-be-tied object 30.

Figure 12:
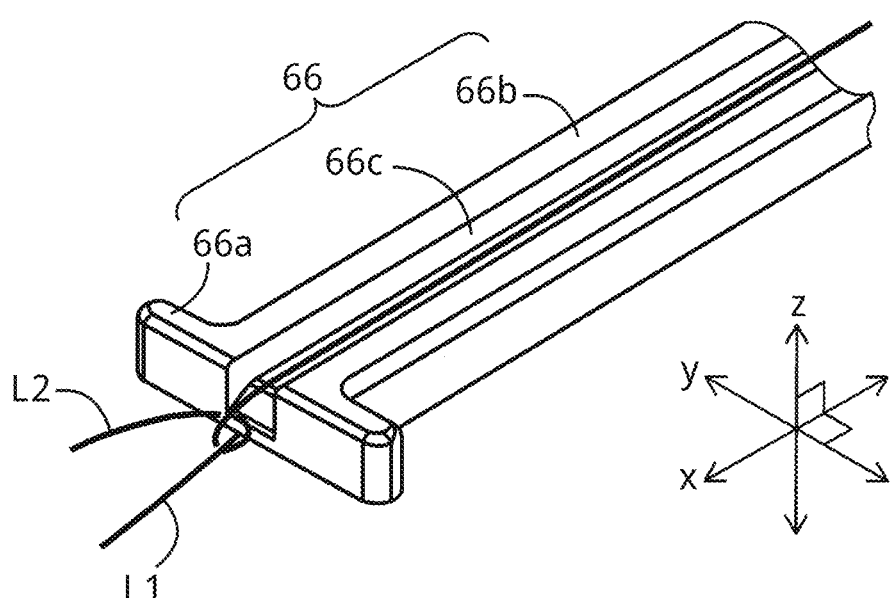
FIG. 12 is a perspective view of a main part of a knot pusher used in the knot tying device of FIG. 1.
Figure 13:
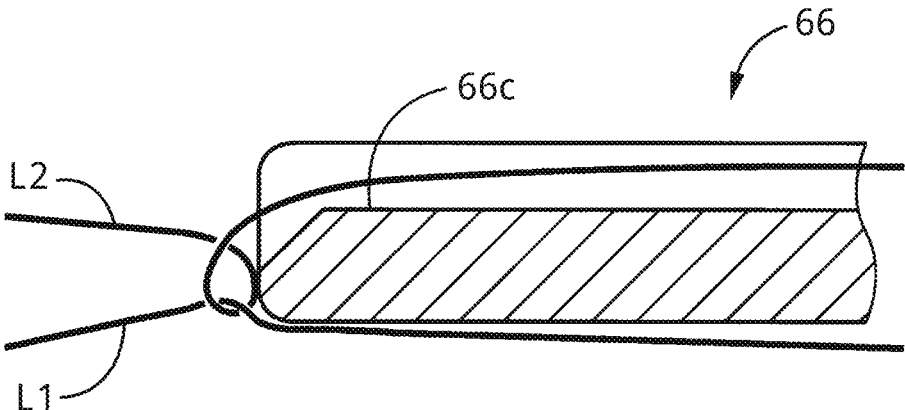
FIG. 13 is a cross-sectional view of the main part of the knot pusher of FIG. 12.

As illustrated in FIGS. 12 and 13, the knot pusher 66 includes a pressing portion 66a, a shaft portion 66b, and a guide groove 66c. The pressing portion 66a is disposed at a distal end of the knot pusher 66 and has a relatively wide width. The shaft portion 66b is contiguous with the pressing portion 66a and has a width less than that of the pressing portion 66a. The guide groove 66c is defined in an upper surface of the pressing portion 66a and an upper surface of the shaft portion 66b in a middle of the pressing portion 66a and the shaft portion 66b in the width direction y and extends in the longitudinal direction x. The knot pusher 66 guides the second suture hook 68 (refer to FIG. 7) along the guide groove 66c in the longitudinal direction x of the knot tying device 10. When the knot pusher 66 pushes the second suture loop LP2, the guide groove 66c catches the suture L. In response to the shaft portion 66b being moved forward, the knot pusher 66 shifts the location of the second suture loop LP2 toward the first suture loop LP1 to form a knot M (refer to FIGS. 39 and 40). After the to-be-tied object 30 in which the knot M has been formed is moved from between the first jaw portion 12 and the second jaw portion 28, the second suture hook 68 is moved forward to catch and hold the suture L extending from the second holding surface 28b of the second jaw portion 28. Thereafter, the second suture hook 68 is moved back ward to engage the suture L with a suture engagement groove 72c of a first suture loop shaft 72 and a suture engagement groove 74c of a second suture loop shaft 74.

Figure 14:
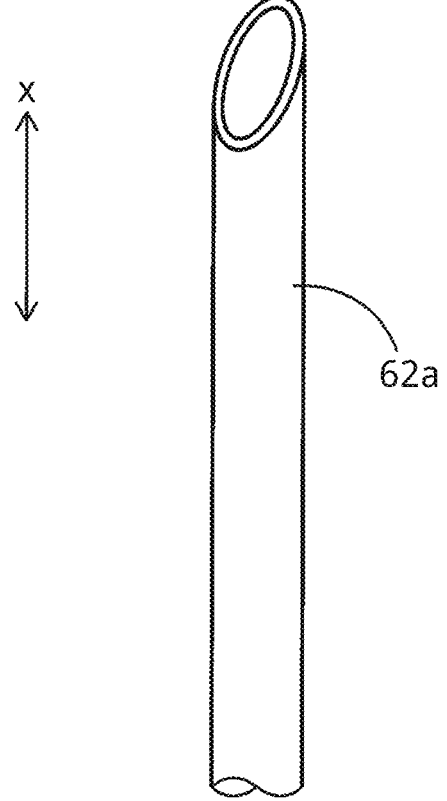
FIG. 14 is a perspective view of an outer cylinder constituting a first suture hook used in the knot tying device of FIG. 1.
Figure 15:
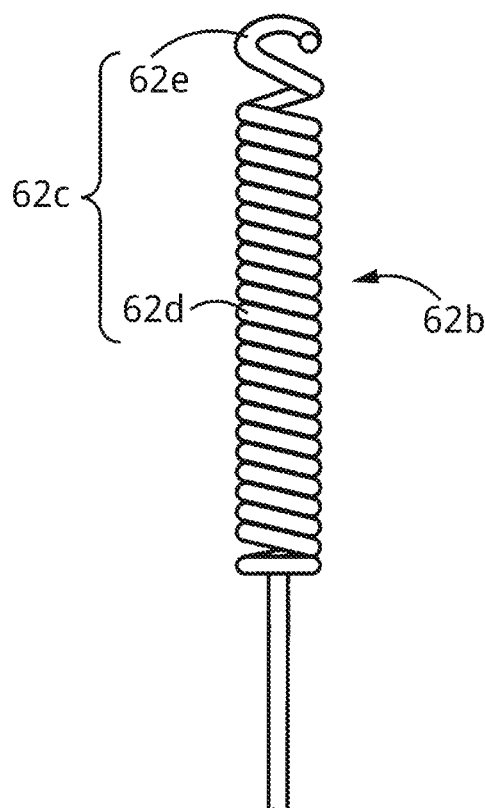
FIG. 15 illustrates a holding operation member accommodated in the outer cylinder of FIG. 14.

The first suture hook 62 includes a longitudinal outer cylinder 62a and a holding operation member 62b. The outer cylinder 62a has an obliquely cut tip as illustrated in FIG. 14. The holding operation member 62b illustrated in FIG. 15 is disposed inside the outer cylinder 62a so as to be slidable in the longitudinal direction x and in a direction in which the holding operation member 62b rotates about its axis. The holding operation member 62b is formed of a single wire rod, and includes a spring portion 62c at its distal end portion. The spring portion 62c is allowed to protrude from a distal end opening of the outer cylinder 62a. The spring portion 62c includes a tightly coiled spring portion 62d and an engagement spring portion 62c. The tightly coiled spring portion 62d is a particular portion of the wire rod, wherein the particular portion is tightly wound in a spiral. The engagement spring portion 62e is contiguous from the tightly coiled spring portion 62d. The engagement spring portion 62d is wound while being spaced from the tightly coiled spring portion 62d. The engagement spring portion 62e is a spring with a return portion with a reverse lead at its distal end portion.

Figure 16:
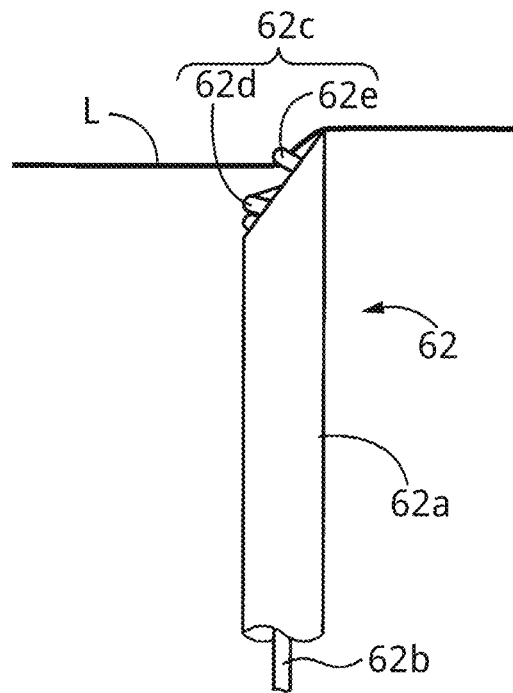
FIG. 16 illustrates the first suture hook in a loosely-holding state, the first suture hook including the outer cylinder of FIG. 14 and the holding operation member of FIG. 15.

FIG. 16 illustrates the first suture hook 62 in the loosely-holding state. In the loosely holding state, the spring portion 62c is located inside the outer cylinder 62a with a portion of the engagement spring portion 62c that is in engagement with the suture L being exposed from the end surface of the outer cylinder 62a. In this loosely-holding state, the first suture hook 62 loosely holds the suture L, and allows the suture L to slide with a certain tension or greater tension.

Figure 17:
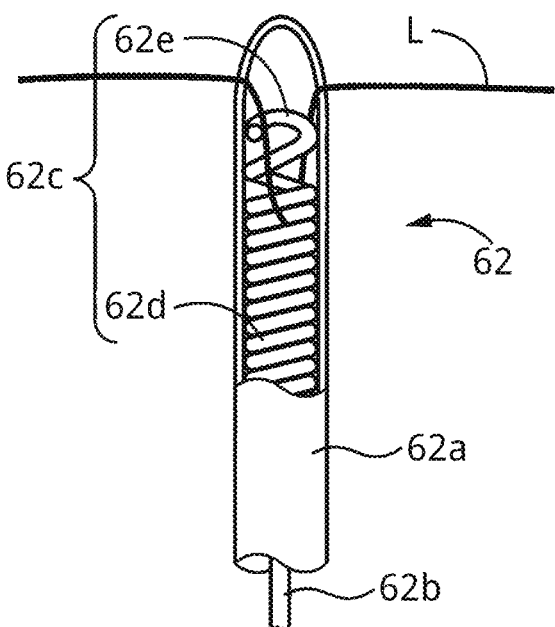
FIG. 17 illustrates the first suture hook in a securely-holding state, the first suture hook including the outer cylinder of FIG. 14 and the holding operation member of FIG. 15.

FIG. 17 illustrates the first suture hook 62 in the securely-holding state. In the securely-holding state, the spring portion 62c is entirely located inside the outer cylinder 62a while the suture L is engaged with the tightly coiled spring portion 62d. In this securely-holding state, the first suture hook 62 securely holds the suture L, and thus does not allow the suture L to slide even when the certain tension or greater tension is applied to the suture L.

Figure 18:
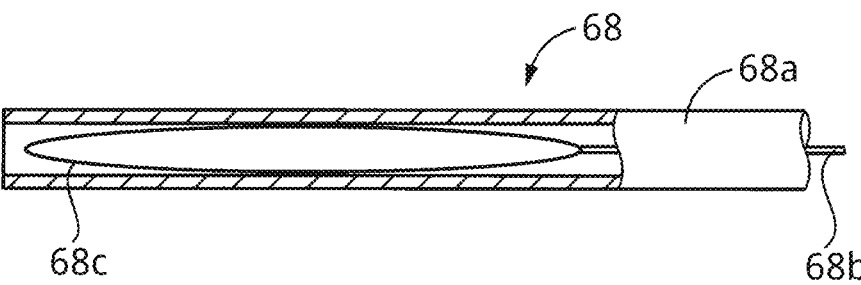
FIG. 18 is a partially cutaway view of a second suture hook used in the knot tying device of FIG. 1, for explaining a configuration of the second suture hook.
Figure 41:
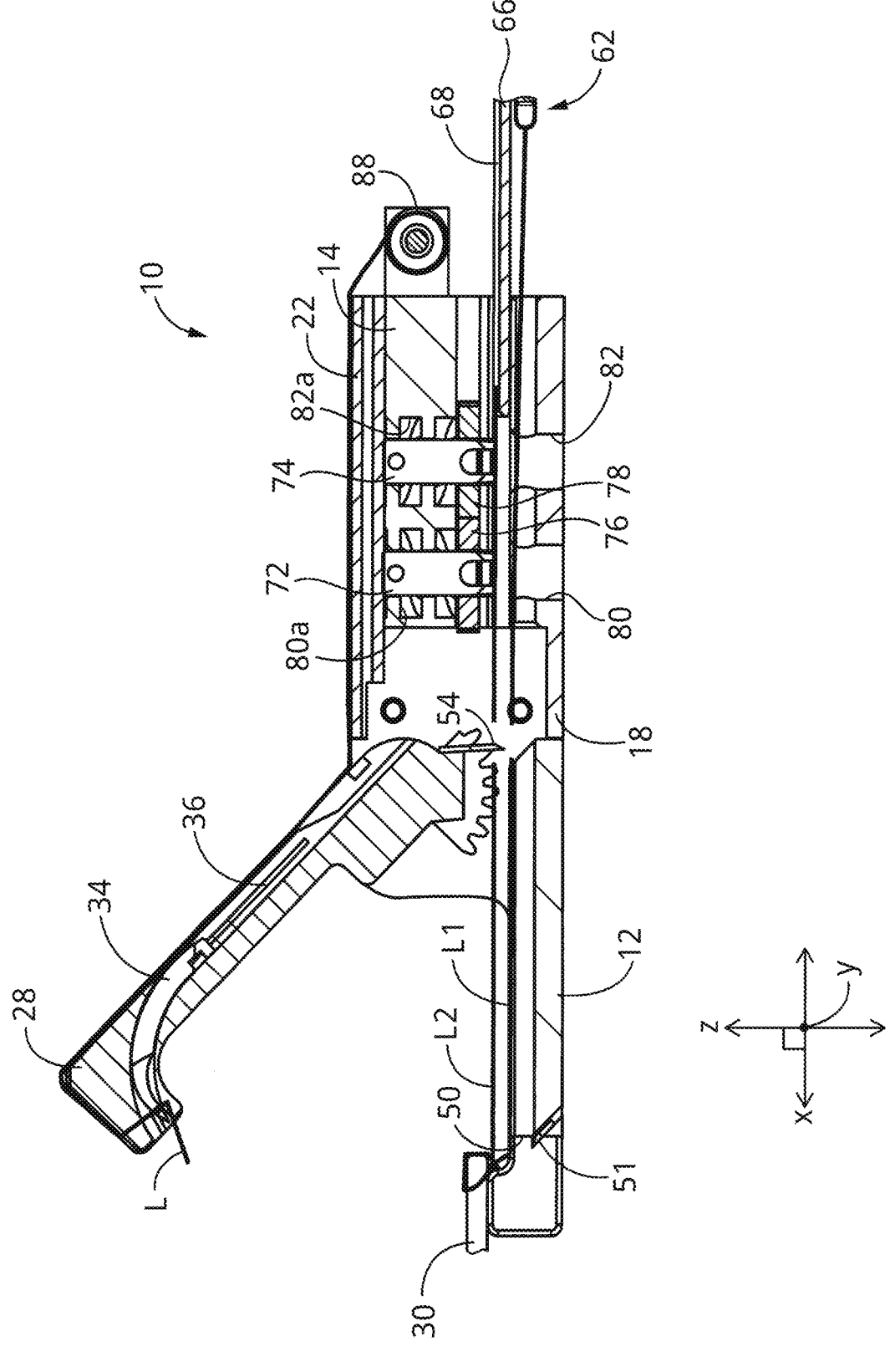
FIG. 41 illustrates a to-be-tied object releasing step in which the second jaw portion is moved away from the first jaw portion to cut the suture at a point between the knot and the first suture hook and a point between the knot and the second suture hook to release the to-be-tied object.

As illustrated in FIG. 18, the second suture hook 68 includes a longitudinal outer cylinder 68a and a wire 68b. The wire 68b is disposed inside the outer cylinder 68a so as to be slidable in the longitudinal direction x. The wire 68b has a wire loop 68c at its distal end. The wire loop 68c allows the suture L to pass therethrough. In response to the wire 68b being moved forward toward the distal end of the second jaw portion 28, the wire loop 68c protrudes from the outer cylinder 68a and thus opens by its elastic restoration as illustrated in FIG. 41.

As illustrated in FIGS. 7, 8, 24 and 25, the knot tying device 10 includes a loop forming portion 71 in the main body 14. The loop forming portion 71 fixedly forms a plurality of loops (e.g., the pair of first suture loop LP1 and second suture loop LP2 in the illustrative embodiment) on the suture L that extends from the needle hole 38 of the curved needle 34 and is pulled by the second suture hook 68.

The loop forming portion 71 includes a first suture loop shaft 72 and a second suture loop shaft 74. As illustrated in detail in FIGS. 13 and 14, the loop forming portion 71 further includes a first gear 76 and a second gear 78. As illustrated in FIG. 8, the main body 14 has a first bearing hole 80 and a second bearing hole 82 that are spaced apart from each other in the longitudinal direction x of the knot tying device 10 and are located parallel to each other in the height direction z. The first suture loop shaft 72 and the second suture loop shaft 74 are engaged in the first bearing hole 80 and the second bearing hole 82, respectively. The first suture loop shaft 72 is rotatable about a first rotation axis C1 and is movable in a first rotation axis C1 direction. The second suture loop shaft 74 is rotatable about a second rotation axis C2 and is movable in a second rotation axis C2 direction. The first rotation axis C1 and the second rotation axis C1 are apart from each other in the longitudinal direction x and parallel to the height direction z. The first suture loop shaft 72 is engaged with a first gear 76 in such a manner that the first suture loop shaft 72 is not rotatable relative to the first gear 76 and is movable in the first rotation axis C1 direction. The second suture loop shaft 74 is engaged with a second gear 78 in such a manner that the second suture loop shaft 74 is not rotatable relative to the second gear 78 and is movable in the second rotation axis C2 direction. The first gear 76 and the second gear 78 are in mesh with each other while the first gear 76 and the second gear 78 are supported by the main body 14 so as not to be movable in the first rotation axis C1 direction and in the second rotation axis C2 direction, respectively. The first gear 76 and the second gear 78 are examples of a driving rotor. The first suture loop shaft 72 and the second suture loop shaft 74 are examples of a rotation shaft of the loop forming portion 71.

Figure 19:
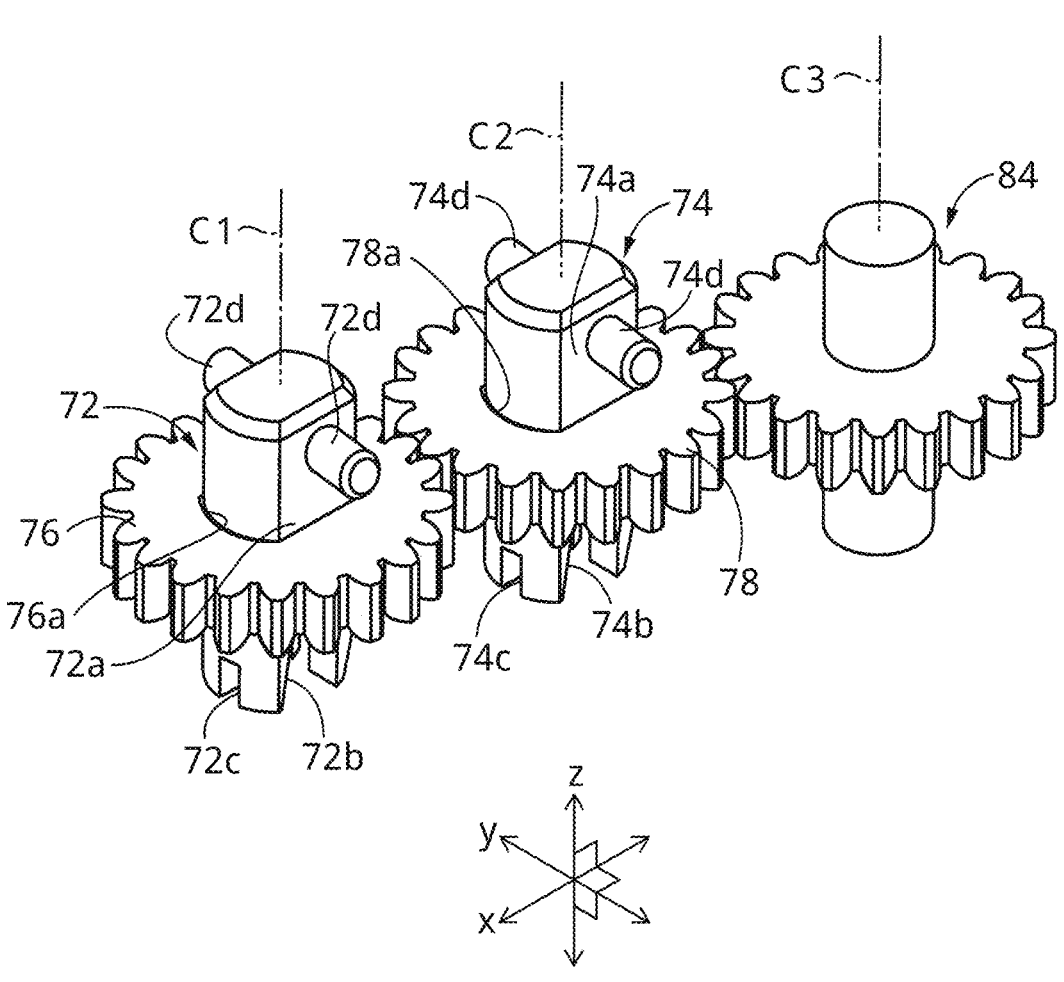
FIG. 19 is a perspective view of a first suture loop shaft and a second suture loop shaft used in the knot tying device of FIG. 1 as viewed obliquely from above.
Figure 20:
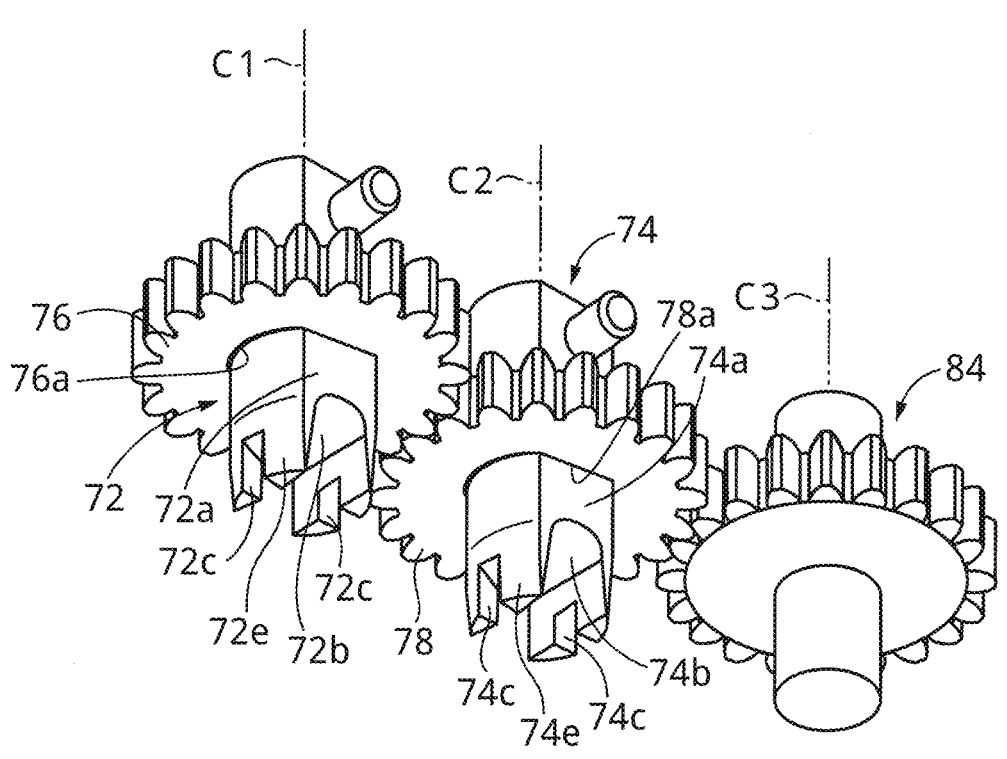
FIG. 20 is a perspective view of the first suture loop shaft and the second suture loop shaft of FIG. 19 as viewed obliquely from below.

As illustrated in FIGS. 19 and 20, the first suture loop shaft 72 has a pair of flat surfaces 72*a* on its outer peripheral surfaces. The flat surfaces 72*a* are opposite to each other with respect to the first rotation axis C1 and extend in the height direction z. The second suture loop shaft 74 has a pair of flat surfaces 74*a* on its outer peripheral surfaces. The flat surfaces 74*a* are opposite to each other with respect to the second rotation axis C2 and extend in the in the height direction z. The first gear 76 has an engagement hole 76*a* having a shape the same as a cross-sectional shape of the first suture loop shaft 72. The second gear 78 has an engagement hole 78*a* having a shape the same as a cross-sectional shape of the second suture loop shaft 74. The first suture loop shaft 72 is engaged with the engagement hole 76*a* of the first gear 76 so as to be movable in the first rotation axis C1 direction. The second suture loop shaft 74 is engaged with the engagement hole 78*a* of the second gear 78 so as to be movable in the second rotation axis C2 direction. The first suture loop shaft 72 has a tapered surface 72*e* at one end portion that is closer to the first lid member 18 than the other end portion thereof, that is, at a lower end portion thereof in FIGS. 19 and 20. The lower end portion of the first suture loop shaft 72 has a diameter that decreases toward the an end of the lower end portion. The second suture loop shaft 74 has a tapered surface 74*c* at one end portion that is closer to the first lid member 18 than the other end portion thereof, that is, at a lower end portion thereof in FIGS. 19 and 20. The lower end portion of the second suture loop shaft 74 has a diameter that decreases toward the an end of the lower end portion.

The first suture loop shaft 72 has a hook groove 72*b* and a suture engagement groove 72*c* at the one end closer to the first lid member 18 than the other end. The hook groove 72*b* has a U-shaped cross section and extends through the one end portion of the first suture loop shaft 72 in a direction orthogonal to the first rotation axis C1. This configuration enables the first suture hook 62 to pass therethrough. The suture engagement groove 72*c* extends through the one end portion of the first suture loop shaft 72 in a direction orthogonal to the first rotation axis C1 and orthogonal to the direction in which the hook groove 72*b* extends. The suture engagement groove 72*c* has a depth less than that of the hook groove 72*b*. The hook groove 72*b* and the suture engagement groove 72*c* are cutouts extending, from the one end closer to the first lid member 18 than the other end, in the first rotation axis C1 direction. The cutout depth of the hook groove 72*b* is greater than the cutout dept of the suture engagement groove 72*c*.

As illustrated in FIGS. 7 and 26, a pair of spiral cam grooves 80*a* are defined in an inner peripheral surface of the first bearing hole 80. The first suture loop shaft 72 includes a pair of cam protrusions 72*d* that protrude toward opposite sides from second-lid-member 22 side end portions, respectively, of the flat surfaces 72*a*. The cam protrusions 72*d* are in engagement with the spiral cam grooves 80*a*, respectively. The cam protrusions 72*d* function as cam followers that rotate along the respective spiral cam grooves 80*a*. The first suture loop shaft 72 is configured such that, in response to the first suture loop shaft 72 being rotated about the first rotation axis C1 together with the first gear 76, the cam protrusions 72*d* receive, from the spiral cam grooves 80*a*, a thrust force in the first rotation axis C1 direction toward the first lid member 18, thereby moving toward the first lid member 18 while rotating about the first rotation axis C1. In response to the first suture loop shaft 72 being rotated three-quarters of a turn in this way, the suture L pulled by the second suture hook 68 through the needle hole 38 of the curved needle 34 is wound around an outer peripheral surface of the first suture loop shaft 72, and thus a first suture loop LP1 is fixedly formed.

Figure 9:
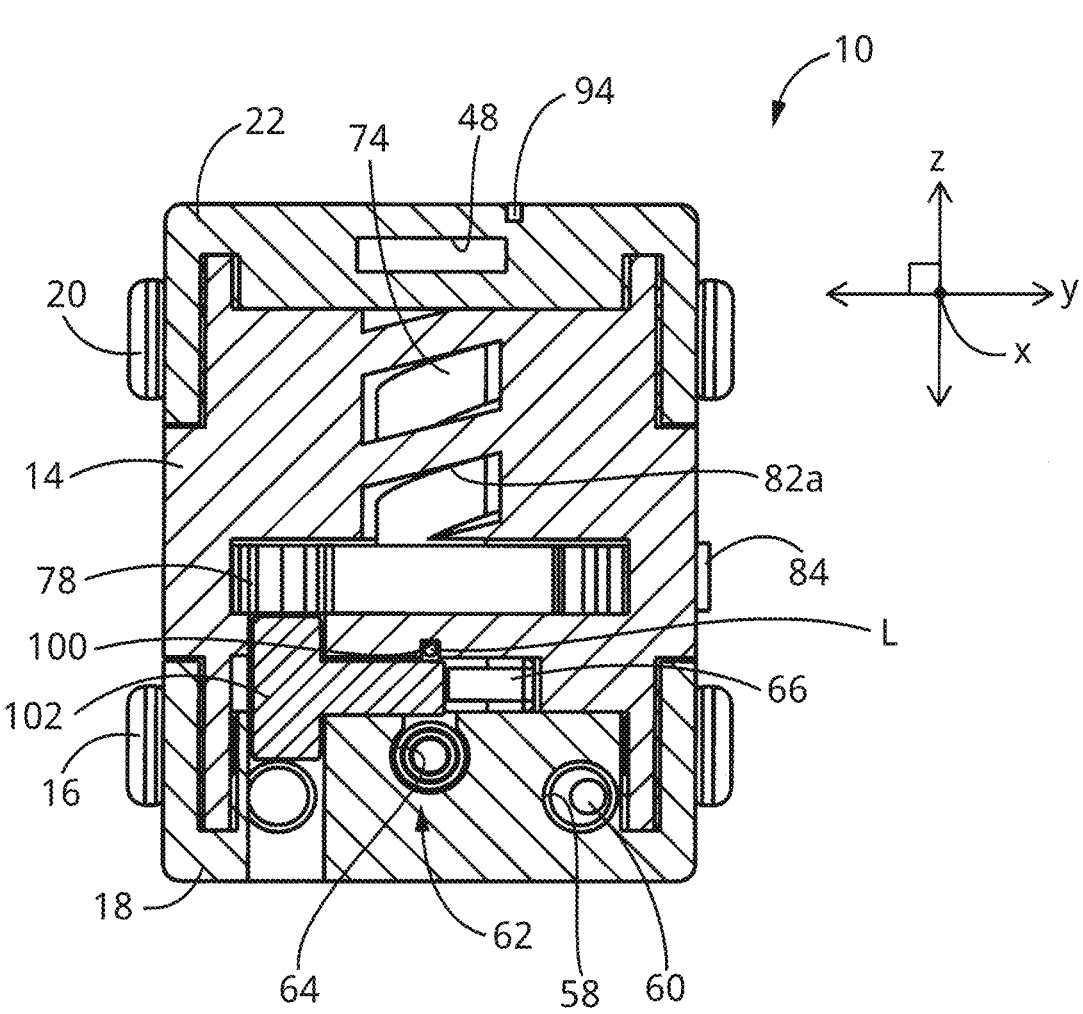
FIG. 9 is a sectional view taken along line C-C of FIG. 3.
Figure 21:
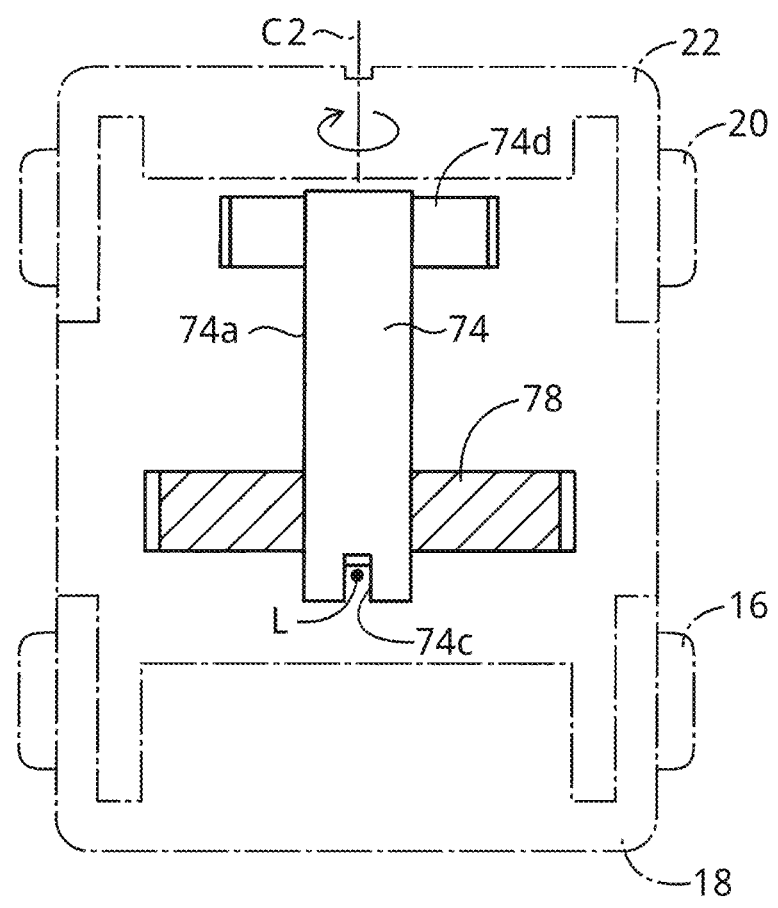
FIG. 21 illustrates the second suture shaft of FIGS. 19 and 20 before the second suture loop shaft is rotated as viewed from the proximal end side of the knot tying device of FIG. 1.
Figure 22:
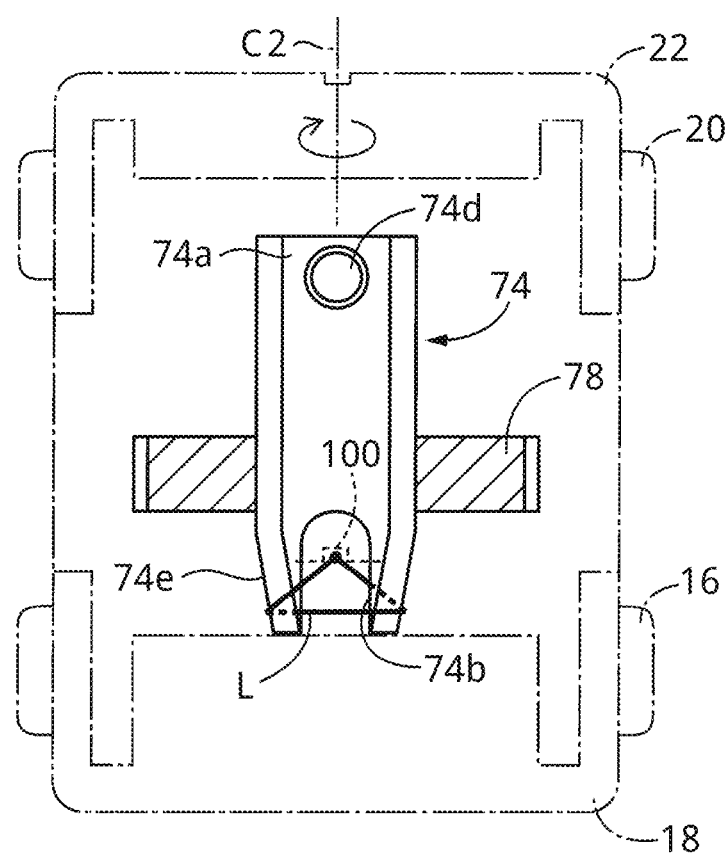
FIG. 22 illustrates a state after the second suture loop shaft is rotated one-quarter of a turn from the state of FIG. 21 as viewed from the proximal-end side of the knot tying device of FIG. 1.
Figure 23:
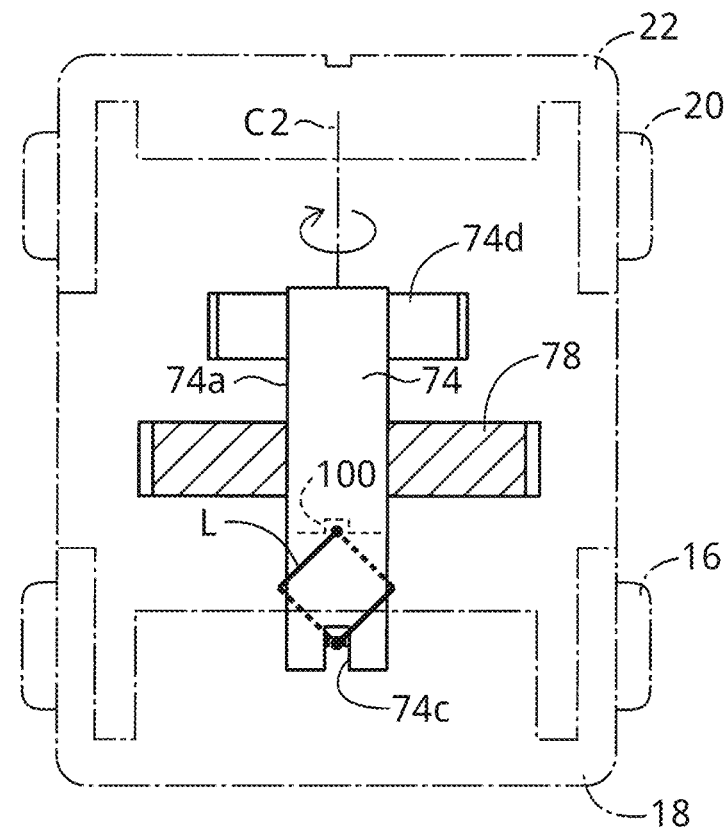
FIG. 23 illustrates a state after the second suture loop shaft is rotated a half of a turn from the state of FIG. 21 as viewed from the proximal-end side of the knot tying device of FIG. 1.
Figure 24:
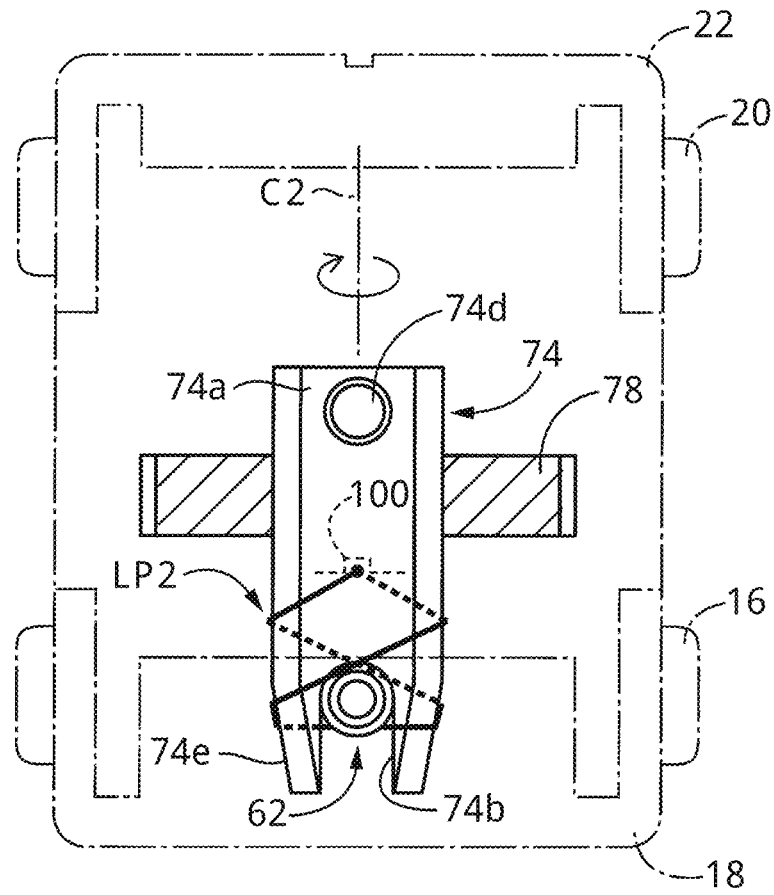
FIG. 24 illustrates a state after the second suture loop shaft is rotated three-quarters of a turn from the state of FIG. 21 as viewed from the proximal-end side of the knot tying device of FIG. 1.

The second suture shaft 74 includes a hook groove 74*b*, a suture engagement groove 74*c*, and a pair of cam protrusions 74*d*. The cam protrusions 74*d* are in engagement with spiral cam grooves 82*a* defined in an inner peripheral surface of the second bearing hole 82, similarly to the first suture loop shaft 72. As illustrated in FIGS. 7, 9, and 26, a pair of the spiral cam grooves 80*a* are defined in the inner peripheral surface of the second bearing hole 82. The spiral direction of the spiral cam grooves 82*a* is opposite to the spiral direction of the spiral cam grooves 80*a*. The cam protrusions 74*d* function as cam followers that rotate along the respective spiral cam grooves 82*a* in a direction opposite to the rotating direction of the cam protrusions 72*d*. The second suture loop shaft 74 is configured such that, in response to the second suture loop shaft 74 being rotated about the second rotation axis C2 together with the second gear 78, the cam protrusions 74*d* receives, from the spiral cam grooves 82*a*, a thrust force in the second rotation axis C2 direction toward the first lid member 18, thereby moving toward the first lid member 18 while rotating about the second rotation axis C2. FIG. 21 illustrates a state when the second gear 78 that has not been rotated. FIG. 22 illustrates a state when the second gear 78 has been rotated one-quarter of a turn from the position of the second gear 78 of FIG. 21. FIG. 23 illustrates a state when the second gear 78 has been rotated a half of a turn from the position of the second gear 78 of FIG. 21. FIG. 24 illustrates a state when the second gear 78 has rotated three-quarters of a turn from the position of the second gear 78 of FIG. 21. In response to the second suture loop shaft 72 being rotated three-quarters of a turn in this way, as illustrated in FIG. 24, the suture L pulled by the second suture hook 68 through the needle hole 38 of the curved needle 34 is wound around an outer peripheral surface of the second suture loop shaft 74, and thus a second suture loop LP2 is fixedly formed (refer to FIG. 24).

An operation gear 84 is disposed in the main body 14 so as to be rotatable about a third axis C3 with being in mesh with the second gear 78. The third axis C3 extends parallel to the first rotation axis C1 and the second rotation axis C2. An outer peripheral portion of the operation gear 84 is partially exposed from an opening 86 (refer FIGS. 1 and 3) defined at a side surface of the main body 14, and is operable. With the configuration described above, a manner of crossing the suture L over itself is opposite to each other between the suture L constituting the first suture loop LP1 and the suture L constituting the second suture loop LP2.

In response to the operation gear 84 being operated toward the proximal end of the knot tying device 10 as indicated by an arrow in FIG. 3, the second gear 78 rotates in a direction opposite to the operation gear 84, and the first gear 76 rotates in the same direction as the operation gear 84. FIGS. 21 to 24 illustrate how the second suture loop shaft 74 operates as viewed from the proximal end side of the knot tying device 10. FIG. 21 illustrates the state before the second suture loop shaft 74 is rotated, wherein the second suture loop shaft 74 is located on a second lid member 22 side (e.g., an upper side along the height direction z in FIG. 21). In FIG. 22, the suture L extending through a fourth suture groove 100 of the main body 14 is threaded through the suture engagement groove 74*c* of the second suture loop shaft 74. FIG. 23 illustrates the state after the second suture loop shaft 74 is rotated, wherein the second suture loop shaft 74 is located on a first lid member 18 side. FIG. 24 illustrates the state in which the second suture loop shaft 74 has been rotated three-quarters clockwise about the second rotation axis C2 to move toward the first lid member 18 while the cam protrusions 74*d* are moving toward the first lid member 18 by receiving a thrust force toward the first lid member 18 from the spiral cam grooves 82*a*. In FIG. 24, a second suture loop LP2 is formed in a state where the suture L is wound around the outer peripheral surface of the second suture loop shaft 74.

The first suture loop shaft 72 is rotated three-quarters counterclockwise about the first rotation axis C1 to move toward the first lid member 18 unlike the second suture loop shaft 74. Nevertheless, as with the second suture loop shaft 74, a first suture loop LP1 is formed in a state where the suture L is wound around the outer peripheral surface of the first suture loop shaft 72, as illustrated in FIGS. 21 to 24.

In this state, in response to the first suture hook 62 being moved toward the distal end, the first suture hook 62 moves along the hook groove 74*b* of the second suture loop shaft 74 and the hook groove 72*b* of the first suture loop shaft 72. As the first suture hook 62 moves as such, the first suture hook 62 passes through the second suture loop LP2 and the first suture loop LP1 that are fixedly formed by being wound around the outer peripheral surfaces of the second suture loop shaft 74 and the first suture loop shaft 72, respectively.

Figure 6:
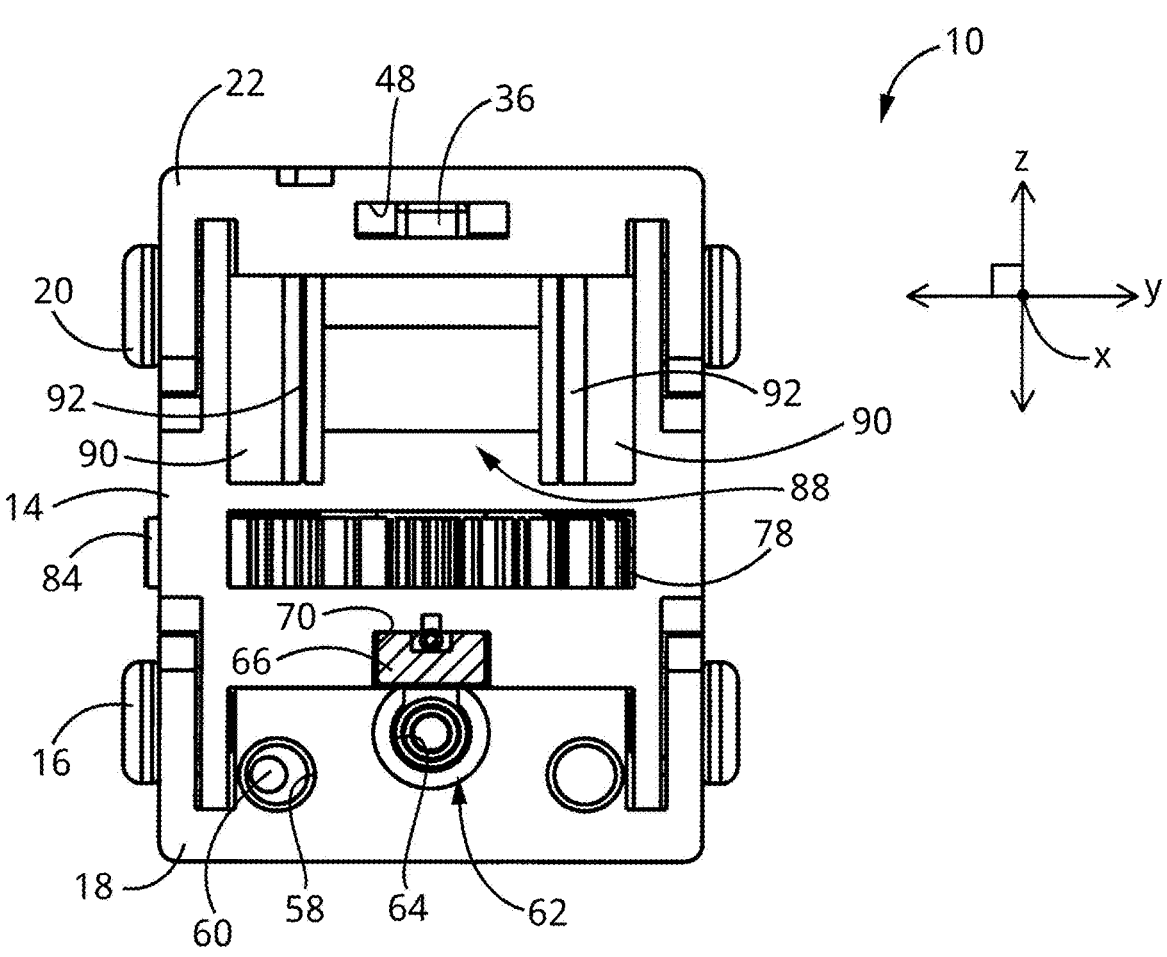
FIG. 6 illustrates the knot tying device of FIG. 1 as viewed from its proximal end.

As illustrated in FIG. 6, the main body 14 includes a pair of brackets 90 at its distal end. The brackets 90 protrude from the distal end of the main body 14 and support a bobbin 88 (an example of a suture supply portion) around which the suture L is wound. A resistance member 92 made of an elastic member such as synthetic rubber or a spring is disposed between the bobbin 88 and each of the brackets 90 to apply rotational resistance to the bobbin 88. The resistance member 92 generates a certain tension in the suture L being drawn from the bobbin 88 in order to prevent the suture L from being loosened.

Figure 4:
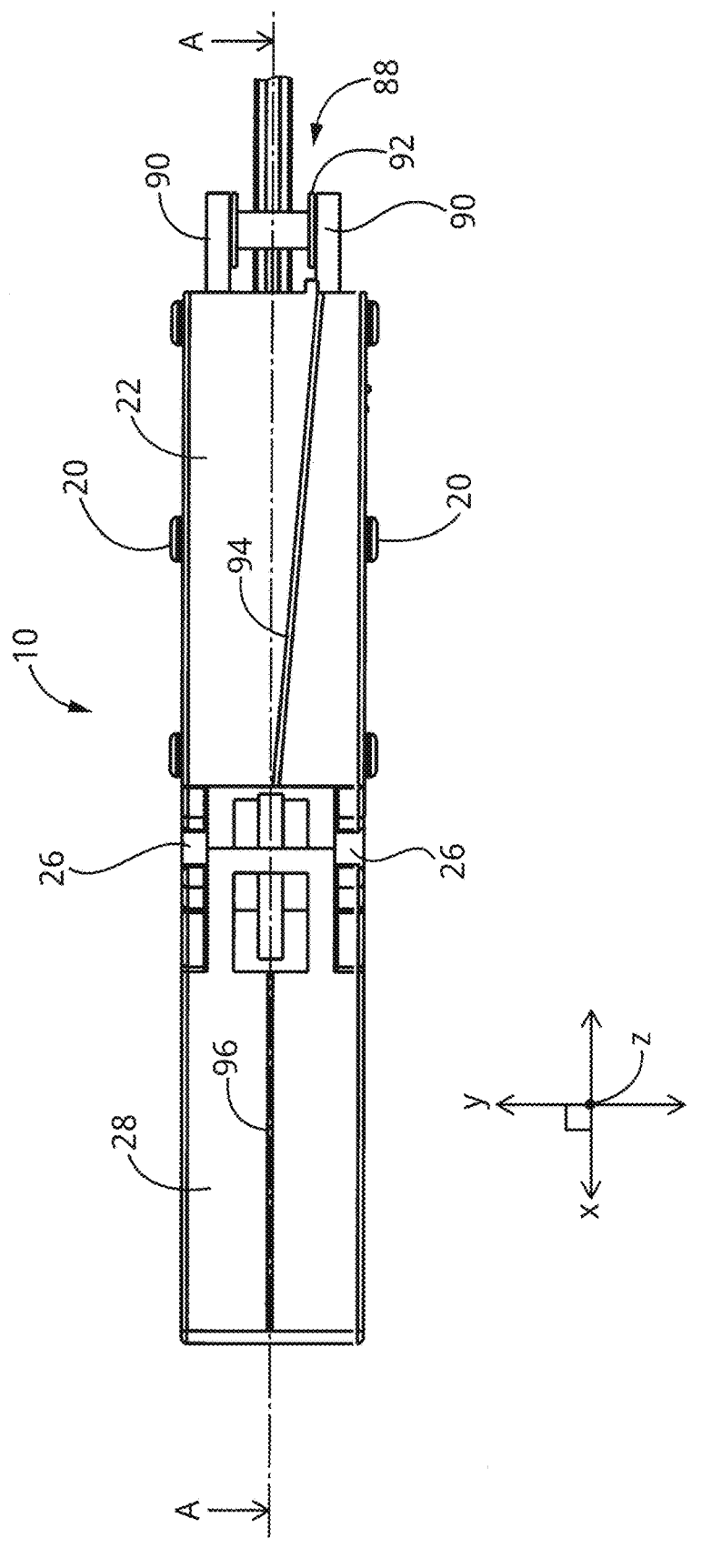
FIG. 4 is a plan view of the knot tying device of FIG. 1.

As illustrated in FIGS. 4 and 5, in order to guide the suture L, a first suture groove 94, a second suture groove 96, a third suture groove 98, and the fourth suture groove 100 are defined at respective positions. The first suture groove 94 is defined in an outer surface of the second lid member 22, which is the surface opposite to the surface facing the main body 14. The second suture groove 96 is defined in an outer surface of the second jaw portion 28. The third suture groove 98 is defined in the distal end surface of the second jaw portion 28. The fourth suture groove 100 is defined in a surface of the main body 14, the surface facing the first lid member 18. The suture L pulled out from the bobbin 88 is guided to the needle hole 38 of the curved needle 34 through the first suture groove 94, the second suture groove 96, and the third suture groove 98 in this order. The suture L that has passed through the needle hole 38 and has been pulled by the second suture hook 68 is positioned in the fourth suture groove 100.

The fourth suture groove 100 is defined in a wall surface of the main body 14, the wall surface defining the second guide hole 70 on the second lid member 22 side, for example, in a middle of an upper wall surface in the width direction y in FIG. 6. The fourth suture groove 100 has a rectangular shape in cross section and has a width less than a width dimension of the second guide hole 70 and a height less than a height of the second guide hole 70.

Figure 25:
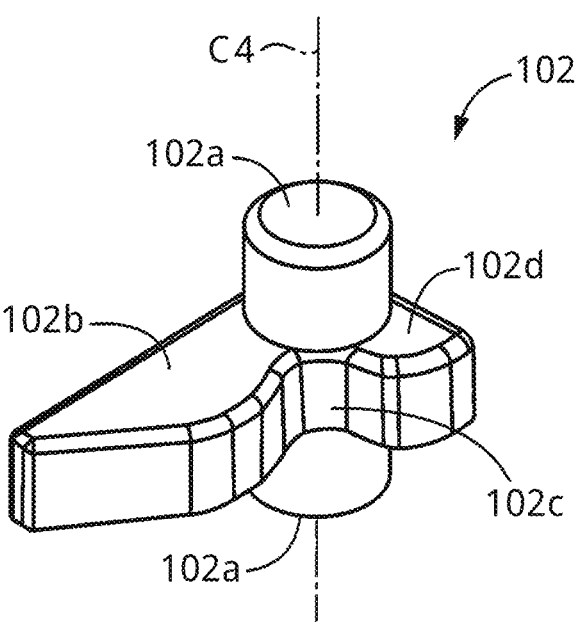
FIG. 25 is a perspective view of a suture presser used in the knot tying device of FIG. 1.

As illustrated in FIG. 8, a suture presser 102 is disposed between the first suture loop shaft 72 and the second suture loop shaft 74 in the longitudinal direction of the main body 14 so as to be rotatable about a fourth axis C4 parallel to the first rotation axis C1 and the second rotation axis C2. As illustrated in FIG. 25, the suture presser 102 includes a pair of shaft portions 102*a*, a relatively long suture pressing portion 102*b*, an engagement recess 102*c*, and an engagement projecting portion 102*d*. The shaft portions 102*a* protrude in a fourth axis C4 direction. The suture pressing portion 102*b* protrudes from the shaft portions 102*a* in a direction orthogonal to the fourth axis C4. The engagement projecting portion 102*d* protrudes from the shaft portions 102*a* such that the engagement projecting portion 102*d* forms an angle of about 90 degrees with respect to the suture pressing portion 102*b* about the fourth axis C4. The engagement recess 102*c* is defined between the suture pressing portion 102*b* and the engagement projecting portion 102*d*.

In response to the knot pusher 66 into which the second suture loop LP2 has been pushed by the engagement projecting portion 102*d* moving backward, the pressing portion 66*a* of the knot pusher 66 pushes the engagement projecting portion 102*d* to rotate the suture presser 102 until longer sides of the suture pressing portion 102*b* extend parallel to the width direction y. At this rotation position, the suture pressing portion 102*b* presses the suture L in the fourth suture groove 100. This prevents slipping of the suture L from the fourth suture groove 100 regardless of the movement of the first suture loop shaft 72 and the second suture loop shaft 74 toward the first lid member 18 in the first rotation axis C1 direction and the second rotation axis C2 direction, respectively, that is, the movement of the first suture loop shaft 72 and the second suture loop shaft 74 toward the loop forming side.

Referring to FIGS. 26 to 45, a description will be provided on a knot tying process performed by the knot tying device 10 configured as described above.

FIG. 26 illustrates a holding preparation step in which the second jaw portion 28 of the knot tying device 10 is separated from the first jaw portion 12 prior to holding a to-be-tied object 30. The suture L is in an initial state. The suture L drawn from the bobbin 88 is guided by the suture grooves 94, 96, and 98 to extend through the needle hole 38 of the curved needle 34 accommodated in the needle housing hollow 32, and is further guided by the suture groove 100. A leading end portion of the suture L guided by the suture groove 100 is held by the second suture hook 68.

Figure 27:
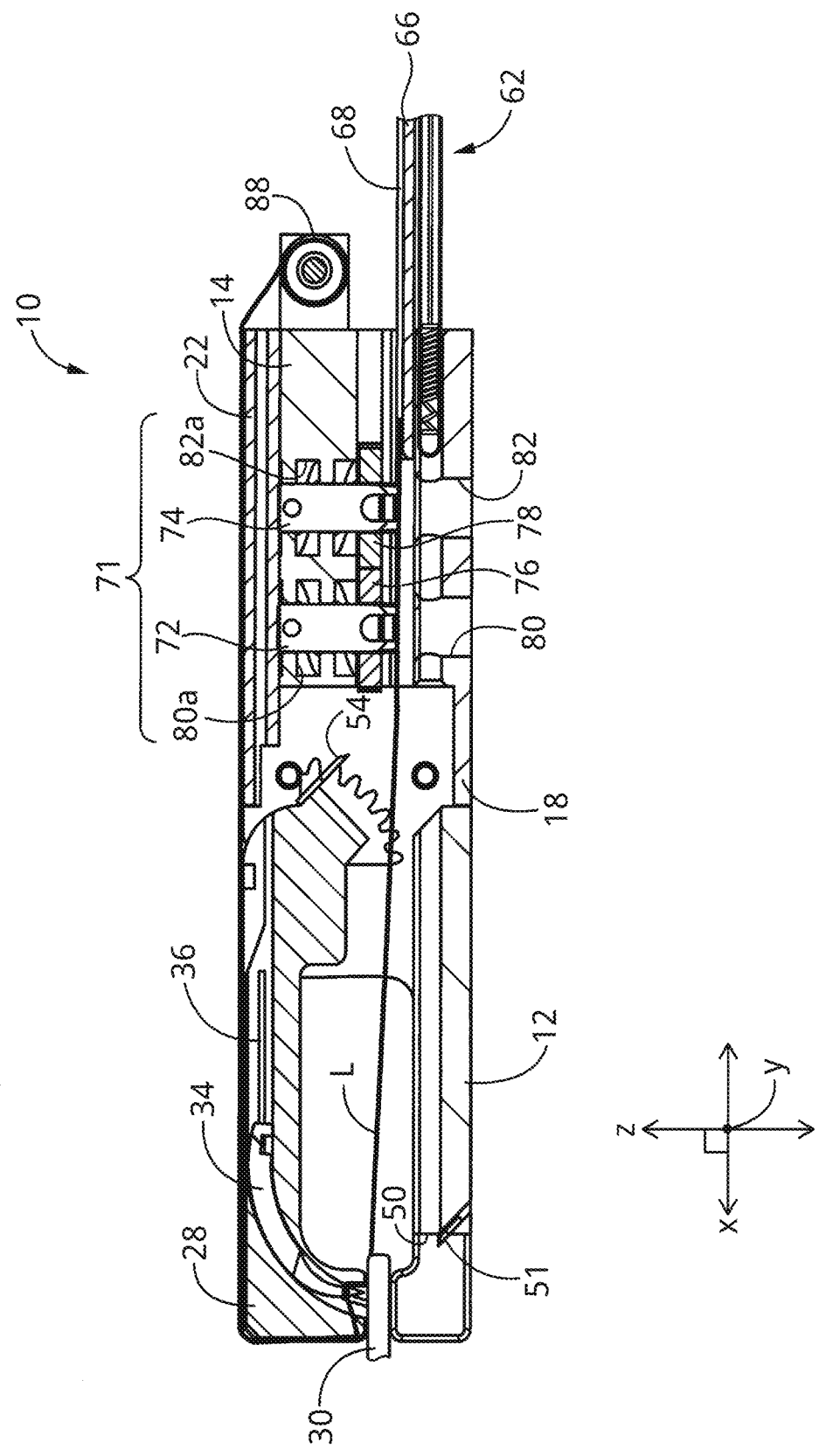
FIG. 27 illustrates a holding preparation step in which the knot tying device of FIG. 1 holds a to-be-tied object at its distal end portion.

Next, in a state where the second jaw portion 28 and the first jaw portion 12 are opened, the opening/closing operation rod 60 is moved toward the proximal end of the needle operating member 36. Thus, in response to movement of the needle operating member 36 toward its distal end, as illustrated in FIG. 27, the second jaw portion 28 is moved toward the first jaw portion 12 in the knot tying device 10, thereby holding the to-be-tied object 30 between the second jaw portion 28 and the first jaw portion 12. FIG. 27 illustrates a holding step in which the to-be-tied object 30 is held.

Then, in response to the operation gear 84 being operated in the direction indicated by the arrow in FIG. 3, the suture L is wound around the outer peripheral surface of the first suture loop shaft 72 moving toward the first lid member 18 while rotating to fixedly form a first suture loop LP1, and the suture L is also wound around the outer peripheral surface of the second suture loop shaft 74 moving toward the first lid member 18 while rotating to fixedly form a second suture loop LP2, as illustrated shown in FIGS. 21 to 24. FIG. 28 illustrates a loop forming step.

Next, in a state where the to-be-tied object 30 is held between the second jaw portion 28 and the first jaw portion 12, the needle operating member 36 is operated to move toward its distal end to a specific position. As a result, as illustrated in FIG. 28, a distal end portion of the curved needle 34 is caused to penetrate the to-be-tied object 30 together with the suture L. In this state, the suture L straightly extends between the needle hole 38 and the to-be-tied object 30, and thus, a gap S is left between the suture L and the recessed portion 40 the distal end portion of the curved needle 34, which enables the first suture hook 62 to hold the suture L readily. FIG. 28 illustrates a needle penetrating step in which the distal end portion of the curved needle 34 is caused to penetrate the to-be-tied object 30 together with the suture L. As indicated by a broken line in FIG. 28, the curved needle 34 is operated to be located at the specific position such that at least a portion of the to-be-tied object 30 is located in a first plane space SP1 defined by the suture L forming two straight lines extending between the needle hole 38 of the curved needle 34 and a location of the first suture loop LP1 and a virtual straight line connecting the needle hole 38 and the location of the first suture loop LP1.

Figure 29:
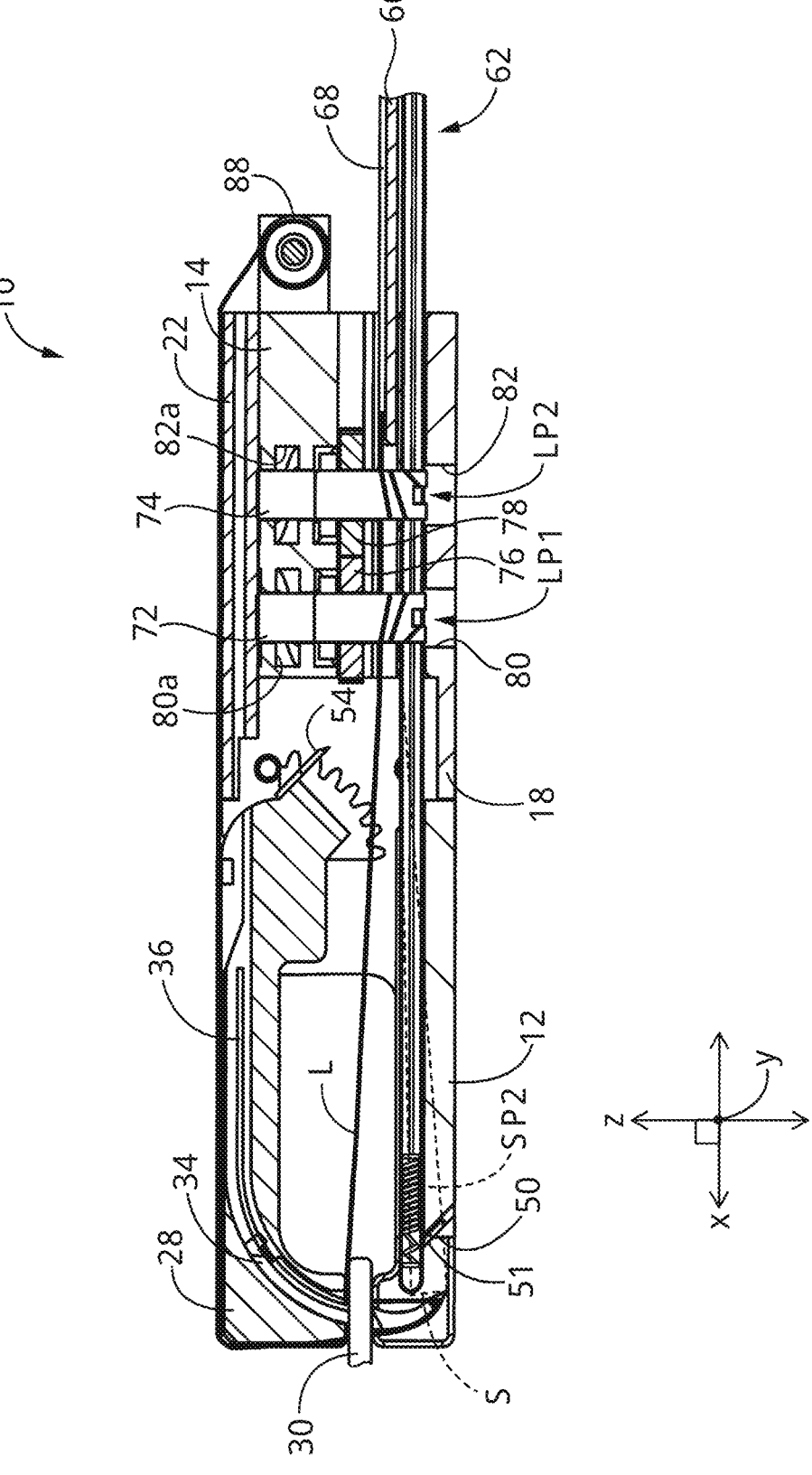
FIG. 29 illustrates a first suture hook holding step in which, in response to the first suture hook moving toward the distal end of the knot tying device through the first suture loop and the second suture loop, the first suture hook catches and holds the suture extending through the to-be-tied object together with the curved needle penetrating the to-be-tied object in the knot tying device of FIG. 1.

Next, in response to the outer cylinder 62*a* of the first suture hook 62 being moved toward the distal end of the knot tying device 10, the outer cylinder 62*a* of the first suture hook 62 is caused to reach the suture L, which is spaced by the gap S from the recessed portion 40 defined in the distal end portion of the curved needle 34, through the second suture loop LP2 and the first suture loop LP1. Subsequently, in this state, in response to the holding operation member 62*b* being rotated by a certain rotation amount with respect to the outer cylinder 62*a*, the suture L spaced from the recessed portion 40 by the gap S is loosely held by the first suture hook 62. FIG. 29 illustrates a first suture hook holding step in which the first suture hook 62 passes through the second suture loop LP2 and the first suture loop LP1 and holds the suture L engaged with the distal end portion of the curved needle 34. As indicated by a broken line in FIG. 29, the position where the first suture loop LP1 holds the suture L is specified such that no portion of the to-be-tied object 30 is located within a second plane space SP2 defined by virtual straight lines connecting the needle hole 38 of the curved needle 34, a location of the first suture loop LP1, and a location where the first suture hook 62 holds the suture L.

Next, the first suture hook 62 is moved toward the proximal end of the knot tying device 10 in a state where the curved needle 34 has been operated such that the suture L extending between the needle hole 38 of the curved needle 34 and the distal end portion of the first suture hook 62 is drawn to a position where the suture L does not contact the first cutter 51 within the second holding surface 28*b* of the second jaw portion 28. At this time, the suture L is loosely held by the first suture hook 62 in the loosely holding state as illustrated in FIG. 16, and thus the suture L is supplied from the bobbin 88 in accordance with the movement of the first suture hook 62.

Figure 30:
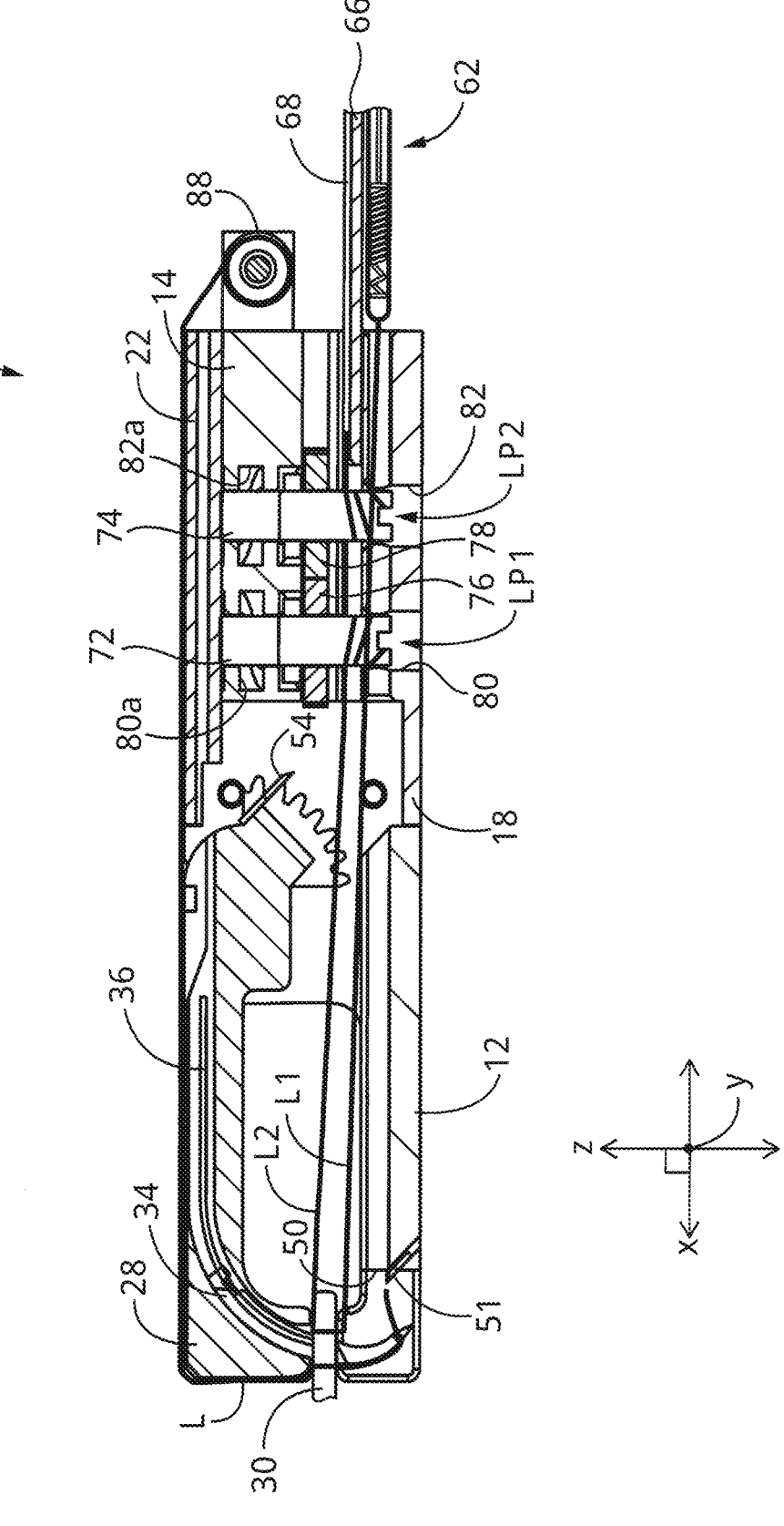
FIG. 30 illustrates a first suture hook backward-moving step in which the suture held by the first suture hook is caused to pass through the first suture loop and the second suture loop in response to the first suture hook moving toward the proximal end of the knot tying device in the knot tying device of FIG. 1, and a cutting step in which the curved needle is caused to further protrude from the to-be-tied object to cause a first cutter to cut the suture in the knot tying device of FIG. 1.

In response to the distal end of the first suture hook 62 having reached between the curved needle 34 and the first suture loop shaft 72, the holding operation member 62*b* of the first suture hook 62 is further rotated, and thus the suture L is held by the first suture hook 62 in the loosely holding state. Thereafter, in response to the first suture hook 62 passing through the first suture loop LP1 and the second suture loop LP2, the suture L is securely held by the first suture hook 62 in the securely-holding state as illustrated in FIG. 17. Then, in this state, the curved needle 34 is moved to further protrude from the second holding surface 28*b* of the second jaw portion 28. Thus, the suture L extending between the needle hole 38 of the curved needle 34 and the distal end of the first suture hook 62 is cut by the first cutter 51. Thereafter, in response to the first suture hook 62 being operated to move toward the proximal end of the knot tying device 10 in parallel to the longitudinal direction x, a first portion L1 of the suture L held by the distal end of the first suture hook 62 is pulled to extend through the first suture loop LP1 and the second suture loop LP2 formed by a second portion L2 of the thread L. FIG. 30 illustrates a backward-moving step of the first suture hook 62 in which the first suture hook 62 pulls the suture L to cause the suture L to extend through the first suture loop LP1 and the second suture loop LP2, and a cutting step of cutting the suture L. In FIG. 30, of suture segments of the suture L separated after cutting by the first cutter 51, one of the suture segments held by the first suture hook 62 and is closer to the first jaw portion 12 than the to-be-tied object 30 is referred to as the first portion L1 of the suture L, and the other of the suture segments held by the second suture hook 68 and is closer to the second jaw portion 28 than the to-be-tied object 30 is referred to as the second portion L2 of the suture L.

The first cutter 51 is disposed at a position where a portion of the suture L extending from the second holding surface 28*b* after the suture L is cut has a sufficient length, that is, the portion of the suture L extending from the needle hole 38 after cutting has a length longer than a distance between the needle hole 38 of the curved needle 34 and the tip of the curved needle 34 and shorter than a distance between the first jaw portion 12 and the second jaw portion 28 that are opened relative to each other at maximum.

Figure 31:
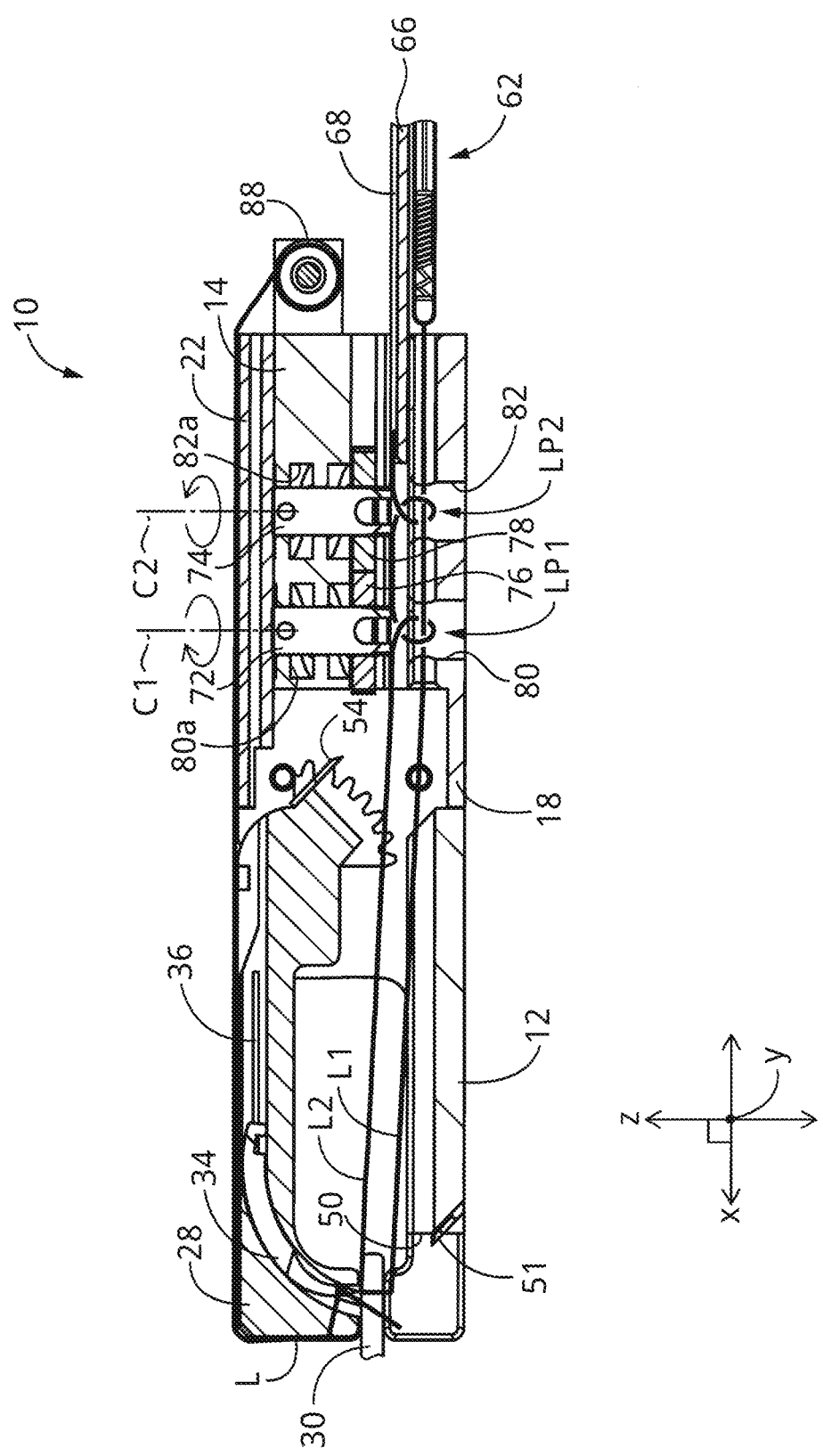
FIG. 31 illustrates a needle retracting step in which the curved needle is retracted in a needle housing hollow and the first suture loop shaft and the second suture loop shaft move toward a second lid member while the first suture loop shaft and the second suture loop shaft are rotating in the knot tying device of FIG. 1.

Then, as illustrated in FIG. 31, in response to the needle operating member 36 being further operated to move toward the proximal end of the knot tying device 10 in parallel to the longitudinal direction x, the curved needle 34 is completely retracted in the needle housing hollow 32 of the second jaw portion 28. As illustrated in FIG. 31, in response to the operation gear 84 being operated in a direction opposite to the arrow in FIG. 3, the first suture loop shaft 72 and the second suture loop shaft 74 are moved toward the second lid member 22. FIG. 31 illustrates a needle retracting step in which the curved needle 34 is retracted in the needle housing hollow 32. In this state, the second portion L2 extending between the first suture loop LP1 and the second suture loop LP2 wound around the first suture loop shaft 72 and the second suture loop shaft 74 is engaged with the suture pressing portion 102*b* of the suture pressure 102, thereby maintaining a suitable loop shape.

Figure 32:
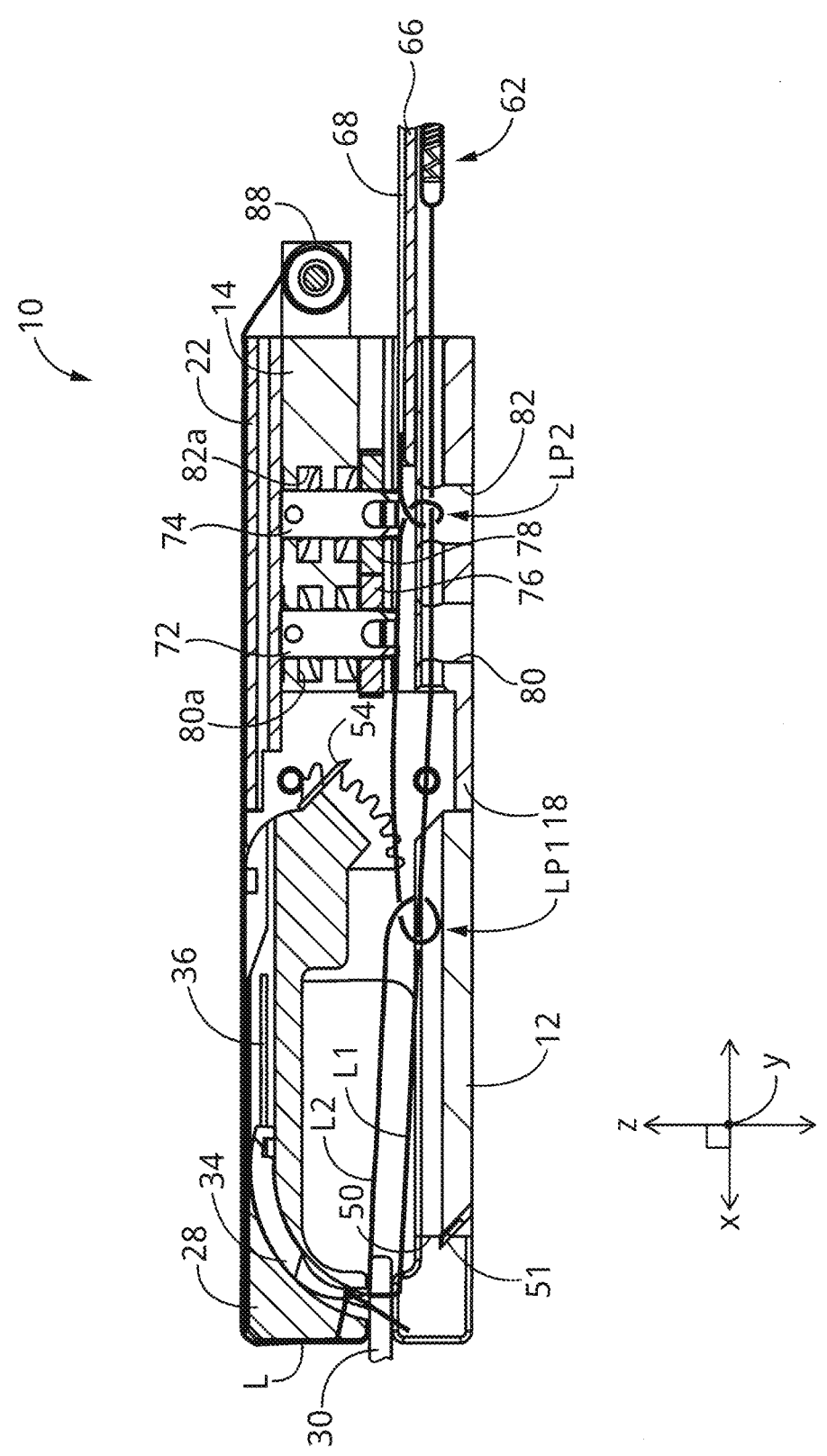
FIG. 32 illustrates a first half action of a first suture loop moving step in which the first suture loop is moved toward the to-be-tied object in response to a first portion of the suture being pulled by the first suture hook in the state of FIG. 31.
Figure 33:
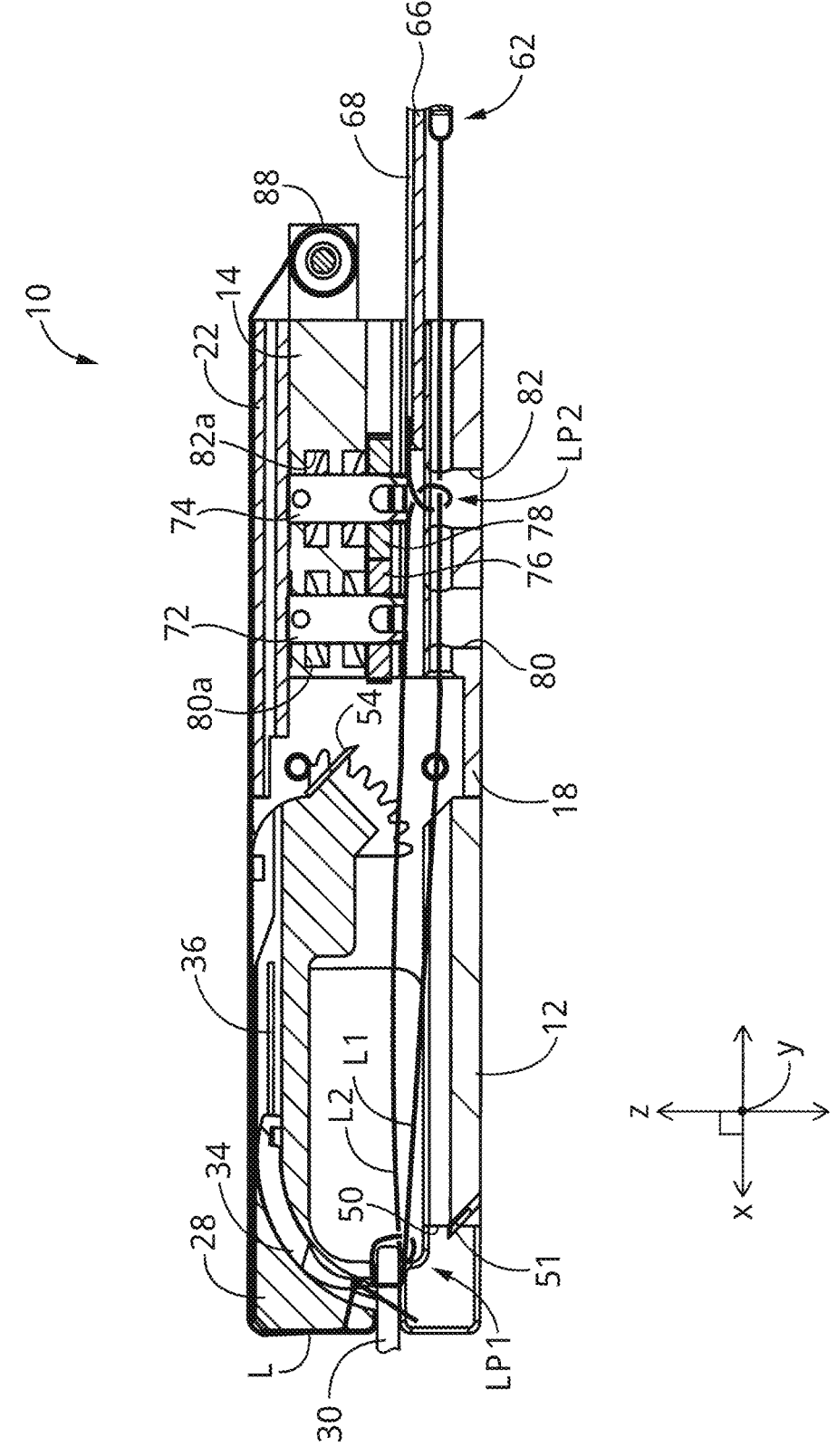
FIG. 33 illustrates a latter half action of the first suture loop moving step in which the first suture loop has reached the to-be-tied object in response to the first portion of the suture being pulled by the first suture hook in the state of FIG. 31.
Figure 34:
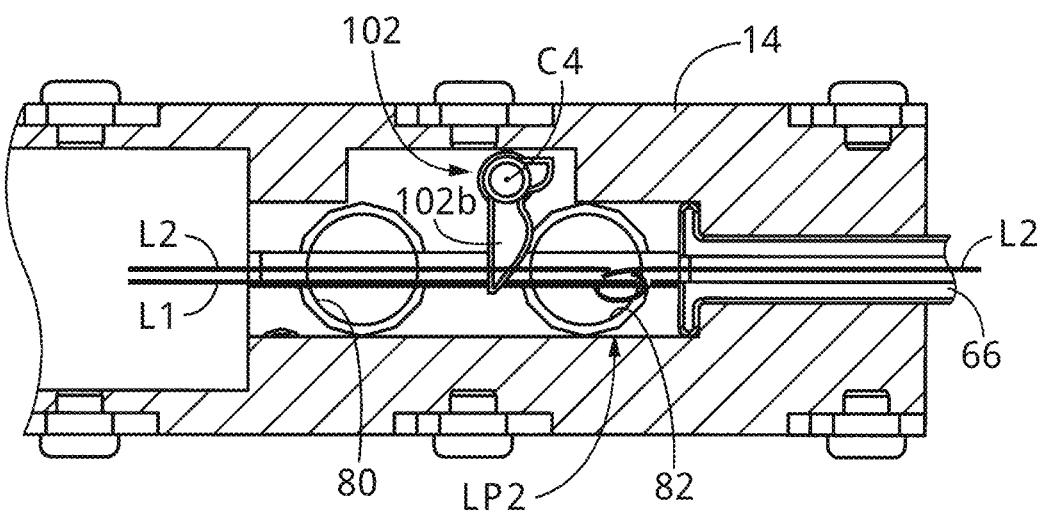
FIG. 34 is a plan view illustrating a relationship between the second suture loop and the knot pusher for pushing the second suture loop in the state of in FIG. 33.
Figure 34:
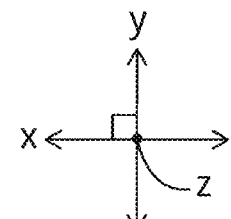

In this state, in response to the suture L being pulled by the first suture hook 62 that is further operated to move toward the proximal end of the knot tying device 10, as illustrated in FIG. 32, of the first suture loop LP1 and the second suture loop LP2, the first suture loop LP1 closest to the to-be-tied object 30 starts to move in a direction toward the to-be-tied object 30. Subsequently, in response to the first suture hook 62 being operated to move toward the proximal end of the knot tying device 10, the first suture loop LP1 reaches the to-be-tied object 30 as illustrated in FIG. 33. FIGS. 32 and 33 illustrates a first suture loop moving step.

After the first suture loop LP1 reaches the to-be-tied object 30, the knot pusher 66 is operated to move toward the distal end of the knot tying device 10, as illustrated in FIGS. 34 to 38. In response to the movement of the knot pusher 66, in a state where a first portion L1 of the suture L is tensioned by the first suture hook 62, the second suture loop LP2 caught by the knot pusher 66 starts to move in a direction toward the to-be-tied object 30, that is, toward the first holding protrusion 12a, along the longitudinal direction x. Until the second suture loop LP2 starts to move by the knot pusher 66, the suture pressing portion 102b of the suture presser 102 holds, in the suture groove 100, the second portion L2 extending between the first suture loop LP1 and the second suture loop LP in the suture L as illustrated shown in FIG. 34, thereby preventing the suture L from disengaging from the suture groove 100.

Figure 35:
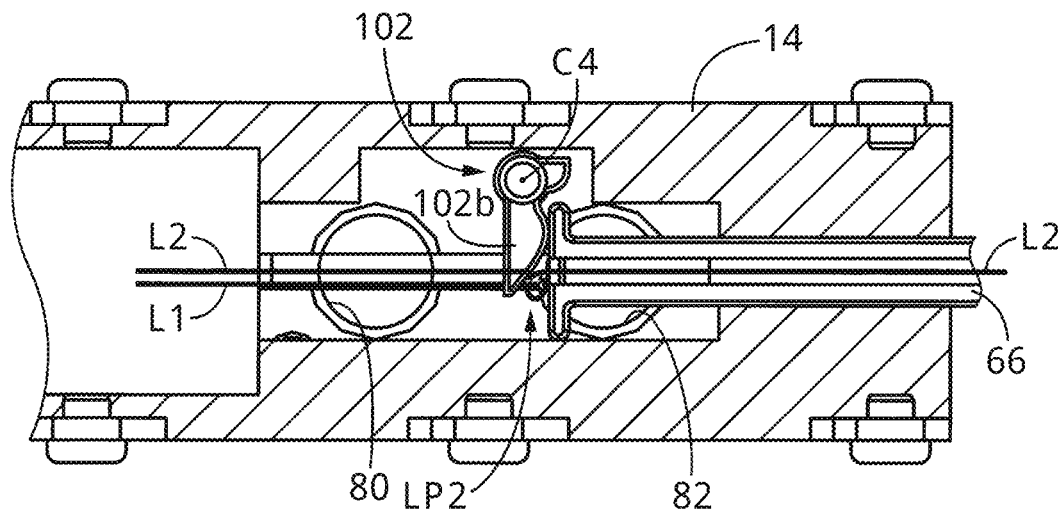
FIG. 35 illustrates a second suture loop moving step in which the knot pusher is in contact with the suture presser while pushing the second suture loop.
Figure 35:
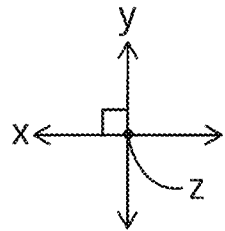
Figure 36:
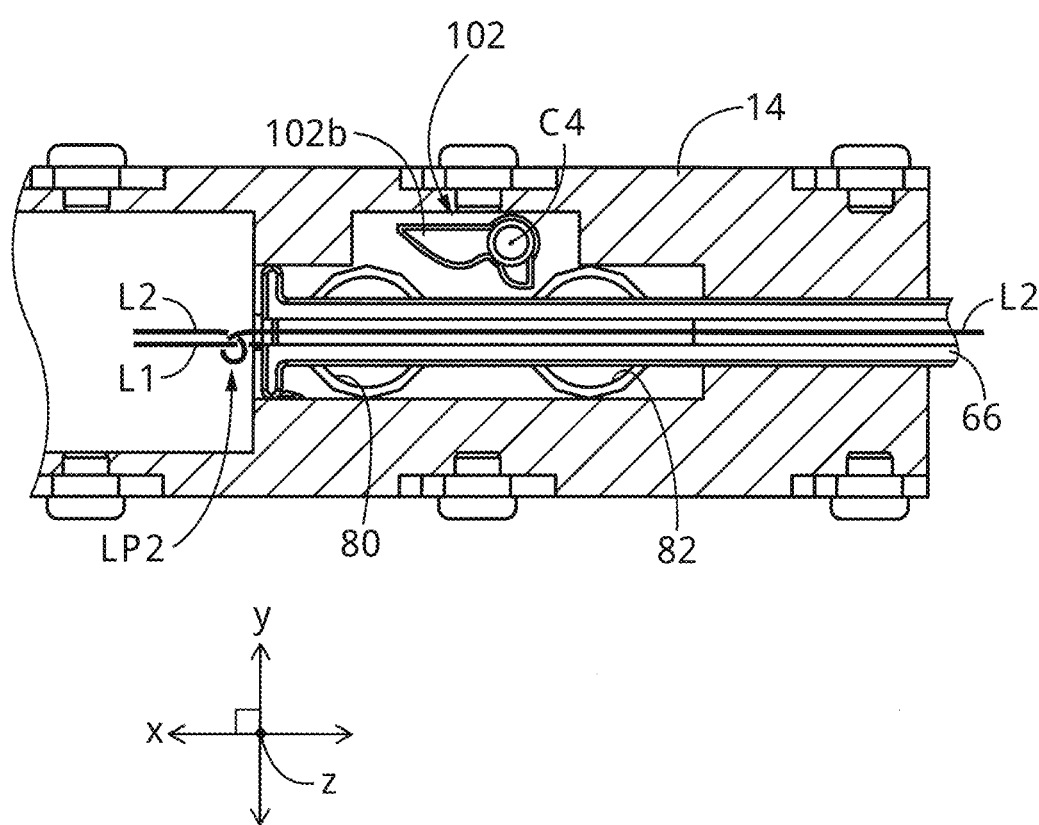
FIG. 36 illustrates the second suture loop moving step in which the knot pusher is further moved to rotate the suture presser about a fourth rotation axis.
Figure 37:
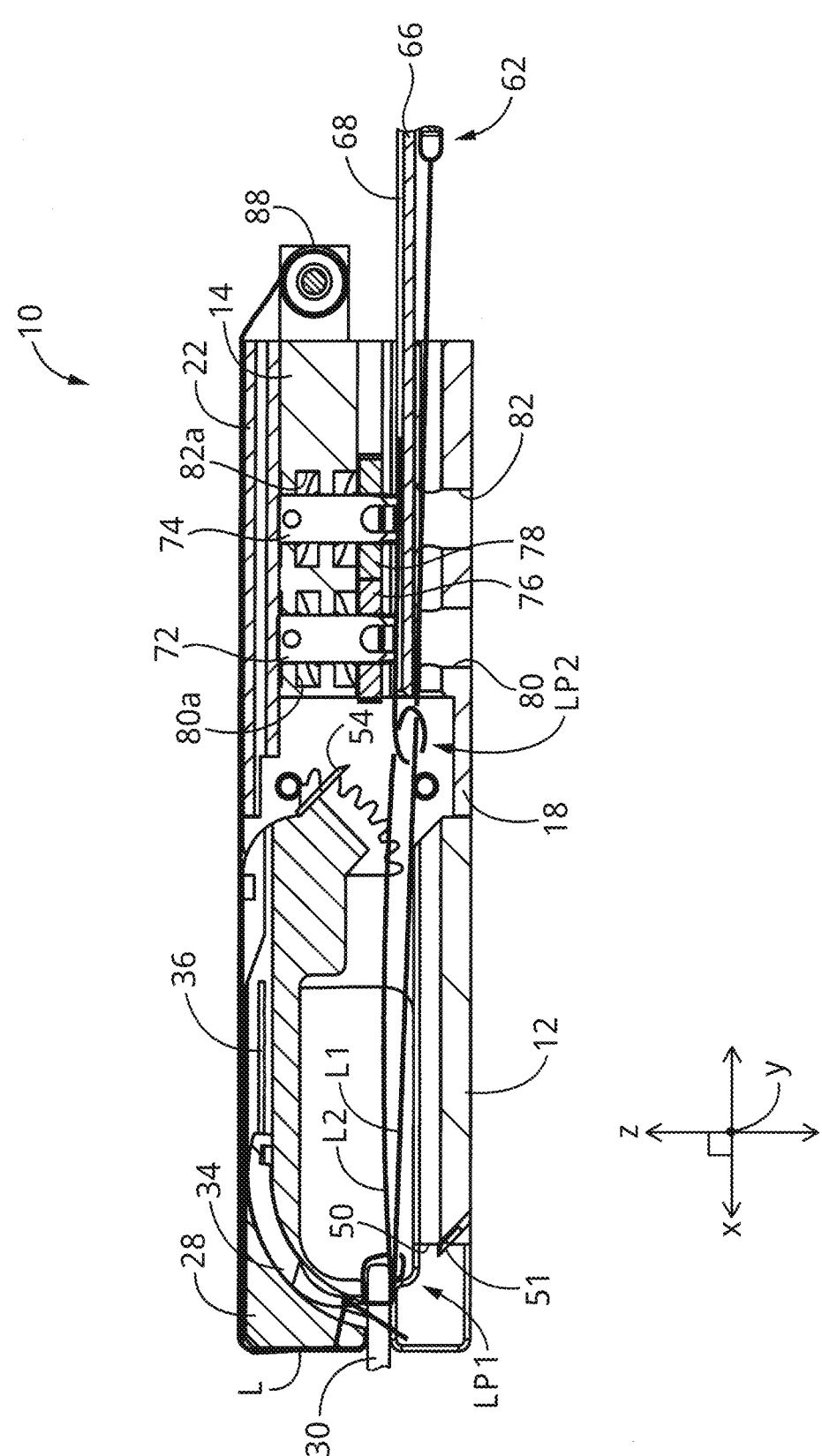
FIG. 37 is a vertical cross-sectional view illustrating the state of FIG. 36 during the second suture loop moving step.
Figure 38:
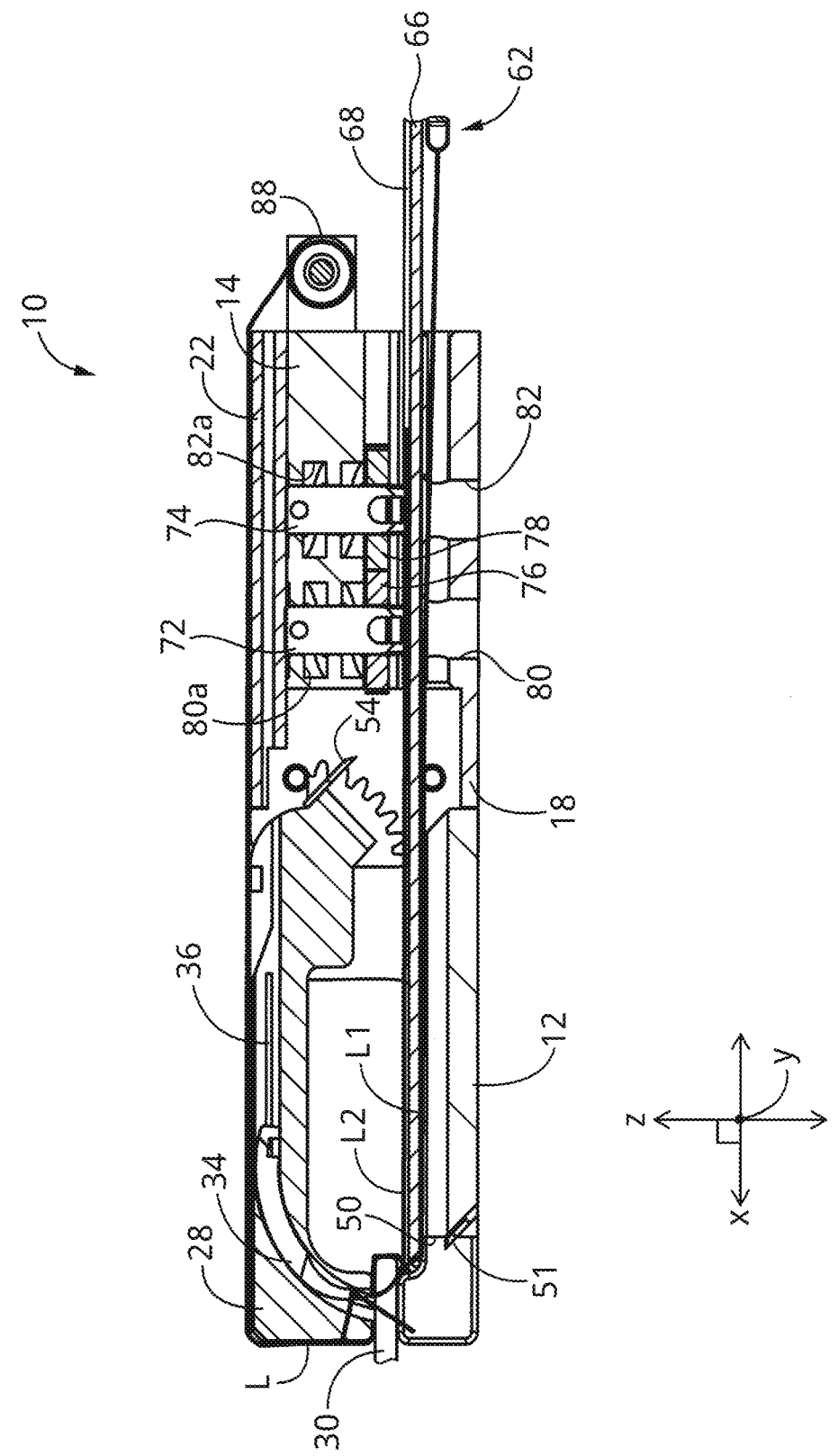
FIG. 38 illustrates the second suture loop moving step in which the second suture loop has reached the to-be-tied object by the movement of the knot pusher during the second suture loop moving step.

While the knot pusher 66 moves forward toward the distal end of the knot tying device 10 with pushing the second suture loop LP2, as illustrated in FIG. 35, the distal end surface of the knot pusher 66 pushes the suture pressing portion 102b of the suture presser 102 toward the distal end of the knot tying device 10. Thus, as illustrated in FIG. 36, the suture presser 102 is rotated about the fourth rotation axis C4, and the second portion L2 extending in the suture groove 100 (refer to FIGS. 7 and 9) becomes free from the pressing by the suture pressing portion 102b. FIG. 37 illustrates this state.

Figure 39:
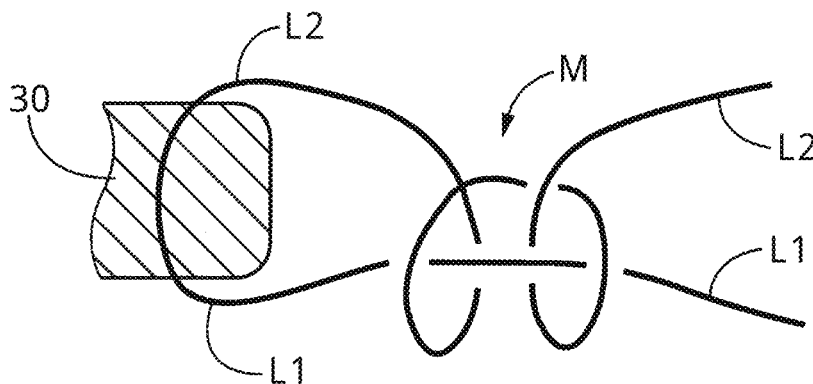
FIG. 39 illustrates a structure of a knot formed by the movement of the second suture loop to the to-be-tied object by the knot pusher, with the suture being loosened.
Figure 40:
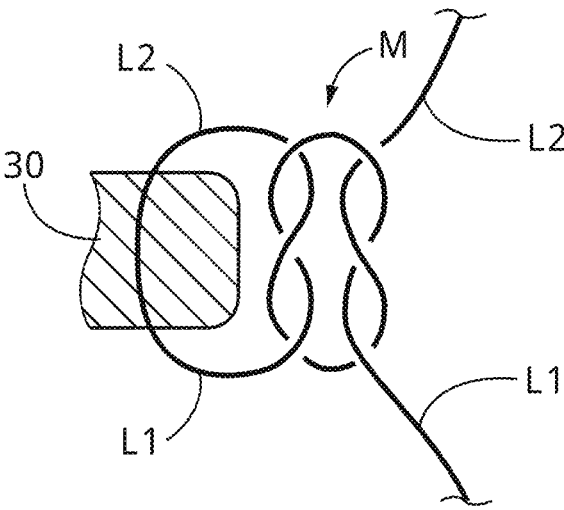
FIG. 40 illustrates a square knot that is one form of the knot of FIG. 39.

In response to the knot pusher 66 being operated to move further toward the distal end of the knot tying device 10, of the first suture loop LP1 and the second suture loop LP2, the second suture loop LP2 that farther from the to-be-tied object 30 than the first suture loop LP1 is, is moved toward the to-be-tied object 30 to be brought into contact with the first suture loop LP. As a result, the first portion L1 located closer to the first jaw portion 12 than the to-be-tied object 30 is and the second portion L2 located closer to the second jaw portion 28 than the to-be-tied object 30 is are tied while being held by the suture hooks 62 and 68, respectively, thereby forming a knot M in the suture L. FIGS. 34 to 38 illustrate a second suture loop moving step. FIG. 39 is an enlarged view of the knot M. FIG. 40 illustrates a square knot that is one form of the knot M further tightened by applying equal tensions to the first portion L1 of the suture L and the second portion L2 of the suture L.

In response to the knot M being formed as described above, as illustrated in FIG. 41, the second jaw portion 28 is rotated to be separated from the first jaw portion 12. This rotation causes the first portion L1 of the suture L and the second portion L2 of the suture L to be cut by the second cutter 54 fixed to the base portion of the second jaw portion 28 and causes the to-be-tied object 30 to be released from the knot tying device 10. FIG. 41 illustrates a to-be-tied object releasing step in which the to-be-tied object 30 in which a knot has been tied using the suture is released from the knot tying device 10.

Figure 42:
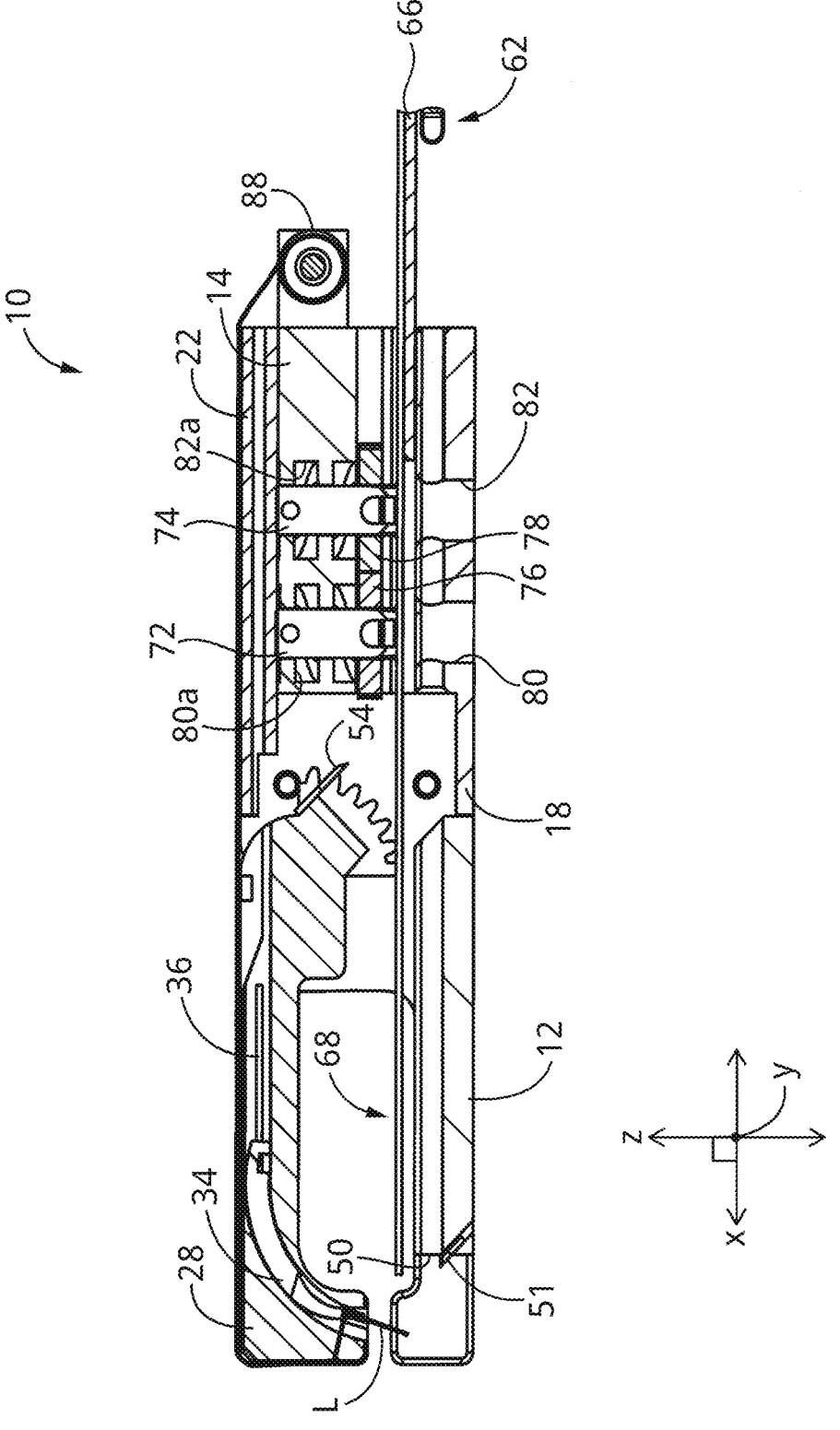
FIG. 42 illustrates a second suture hook in which the second suture hook has been moved toward the distal end of the knot tying device in order to catch and hold a leading end of the suture protruding from the second holding surface of the second jaw portion.

Then, as illustrated in FIG. 42, the second jaw portion 28 is moved toward the first jaw portion 12 until the second jaw portion 28 and the first jaw portion 12 extend parallel to each other and the first holding surface 12b and the second holding surface 28b are slightly spaced apart from each other. Next, the second suture hook 68 is operated to move toward the distal end of the knot tying device 10 such that the distal end of the second suture hook 68 approaches the end of the suture L.

Figure 43:
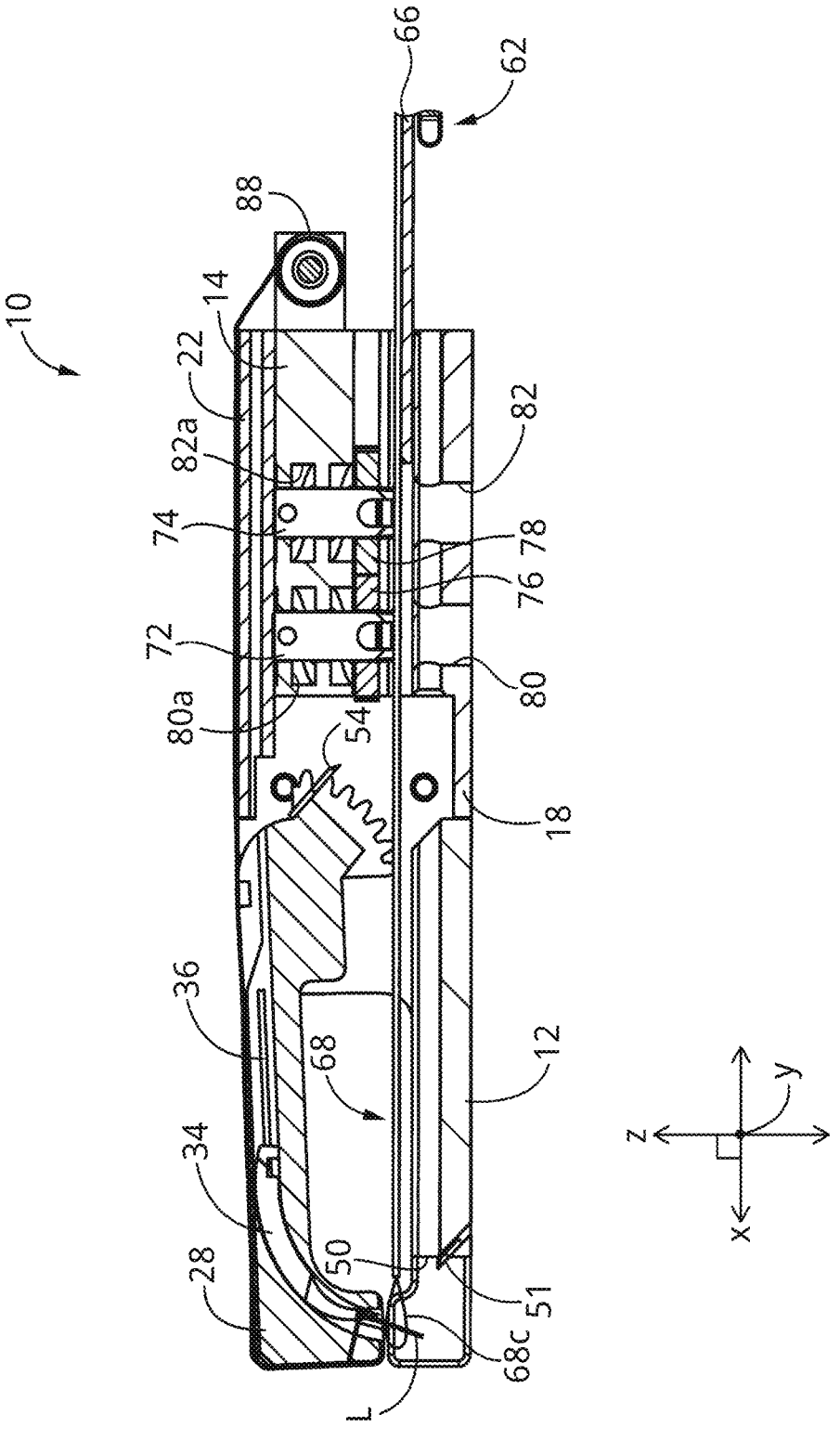
FIG. 43 illustrates the second suture hook holding step in which a wire loop protrudes from a distal end of the second suture hook.

Then, in response to an operation wire 68b being operated to move toward the distal end of the knot tying device 10, the wire loop 68c protruding from the distal end of the second suture hook 68 is placed on the first holding surface 12b of the first jaw portion 12 in a state where the wire loop 68c is expanded to have a width greater than a width of the slot 50. In this state, the second jaw portion 28 is rotated such that the first holding surface 12b and the second holding surface 28b are located adjacent to each other to be almost in contact with each other. In response to the second jaw portion 28 being rotated, a new end portion of the suture L extending from the bobbin 88 and protruding from the second holding surface 28b is threaded into the wire loop 68c protruding from the distal end of the second suture hook 68. FIG. 43 illustrates this state.

Figure 44:
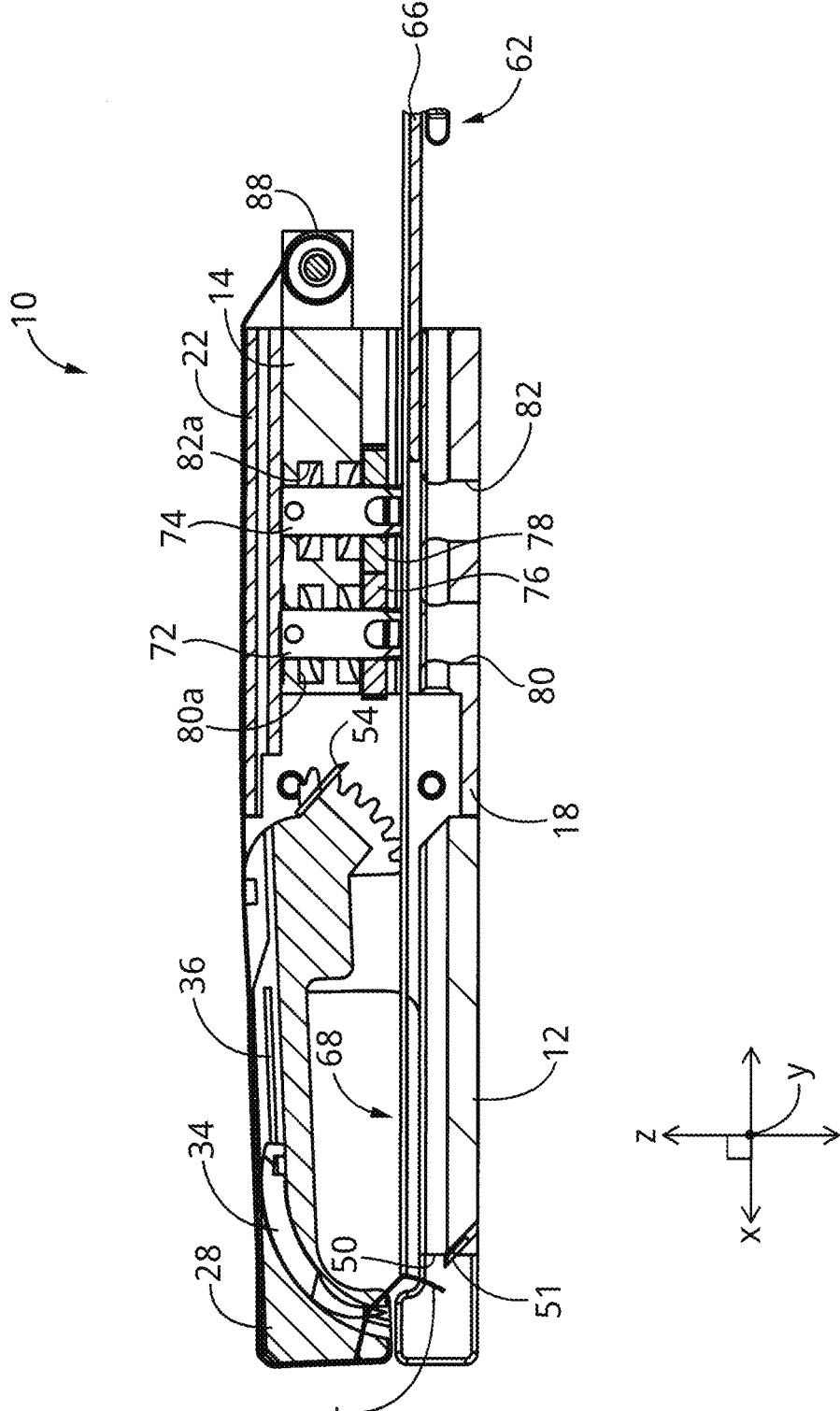
FIG. 44 illustrates the second suture hook holding step in which the leading end of the suture protruding from the second holding surface of the second jaw portion is caught by the second suture hook.

After that, in response to the operation wire 68b being operated to move toward the proximal end of the knot tying device 10, the wire loop 68c is pulled into the outer cylinder 68a. As a result, the end portion of the suture L protruding from the second holding surface 28b of the second jaw portion 28 is held by the distal end of the second suture hook 68, as illustrated shown in FIG. 44. FIGS. 42 to 44 illustrate a second suture hook holding step in which the second suture hook 68 holds the end portion of the suture L protruding from the second holding surface 28b.

Figure 45:
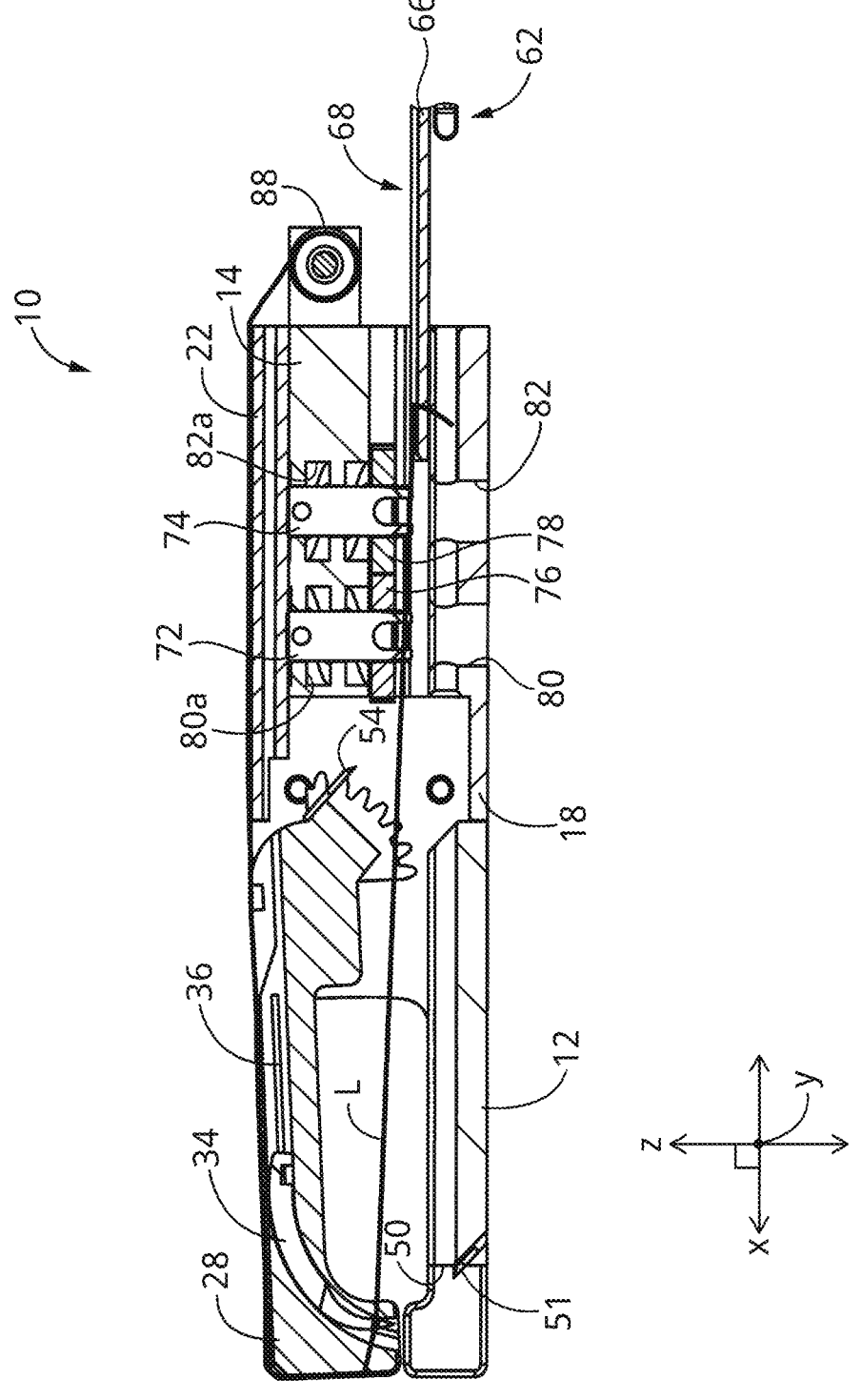
FIG. 45 illustrates a state in which the second suture hook holding the leading end of the suture protruding from the second holding surface of the second jaw portion has been moved toward the proximal end of the knot tying device.

In response to the second suture hook 68 being operated to move toward the proximal end of the knot tying device 10, as illustrated in FIG. 45, the new end portion of the suture L passing through the needle hole 38 of the curved needle 34 accommodated in the needle housing hollow 32 is positioned in the suture groove 100. In this operation section, the suture L is supplied from the bobbin 88. This state is the same as the initial state of FIG. 27 with respect to the suture L. In response to the second jaw portion 28 being separated from the first jaw portion 12, the suture L is in the state of FIG. 26, and knot tying may be performed successively. FIG. 45 illustrates a knot-tying end step in which a single knot-tying action is finished.

As described above, according to the knot tying device 10 of the illustrative embodiment, the first suture hook 62 passes through the first suture loop LP1 and the second suture loop LP2 fixedly formed by the loop forming portion 71. Then, the first suture hook 62 catches and holds the suture L in a state where the needle hole (e.g., suture hooking portion) 38 through which the suture L is threaded is located at the specific position where the needle hole exposed from the to-be-tied object 30. Then, in response to the suture L, which is held by the first suture hook 62, passing through the first suture loop LP1 and the second suture loop LP2, the suture L is tied. The first suture loop LP1 and the second suture loop LP2 are fixedly formed by the loop forming portion 71. Thus, the first suture loop LP1 and the second suture loop LP2 are reliably formed without being affected by, for example, a surface tension of body fluids, a weight of attached body fluids, or other matters. Further, the first suture loop LP1 and the second suture loop LP2 are reliably formed, and thus a knot is reliably tied in the suture L.

According to the knot tying device 10 of the illustrative embodiment, the positioning portion that causes the needle hole (e.g., the suture hooking portion) 38 to be located at the specific position such that at least a portion of the to-be-tied object 30 is located within the virtual first plane space SP1. The first plane space SP1 is defined by the suture L extending between the needle hole (e.g., the suture hooking portion) 38 via the to-be-tied object 30 and the virtual straight lines connecting the needle hole (e.g., the suture hooking portion) 38 and the position of the suture loops. The first suture hook 62 holds the suture L such that no portion of the to-be-tied object 30 is located within the virtual second plane space SP2. The second plane space SP2 is defined by the virtual straight lines connecting the needle hole (e.g., the suture hooking portion) 38, the locations of the suture loops, and the location where the first suture hook 62 holds the suture L. The suture L is then tied in a state where the suture L is placed around at least a portion of the to-be-tied object 30. Thus, a knot may be more reliably tied in the to-be-tied object 30 using the suture L.

According to the knot tying device 10 of the illustrative embodiment, the knot tying device 10 includes the second suture hook 68 and the first cutter 51. The second suture hook 68 holds the end portion of the suture L. The first end portion is the end portion of the suture L that has been threaded into the needle hole (e.g., the suture hooking portion) 38. The first cutter 51 cuts the suture L into a first suture segment L and a second suture segment L after the needle hole (e.g., the suture hooking portion) 38 is located at the specific position where the needle hole is exposed from the to-be-tied object 30 in a state where the first end portion of the suture L is held by the second suture hook 68. In a state where the first suture segment L of the suture L that has been separated from the second suture segment L by cutting by the first cutter 51 is held by the suture hooks 62 and 68, a knot is tied in the first suture segment L. More specifically, a knot is tied in the first suture segment L in a state where one end of the first suture segment L is held by the first suture hook 62 and the other end of the first suture segment L is held by the second suture hook 68. After the knot is tied in the first suture segment L, the second suture hook 68 catches and holds an end portion of the second suture segment L separated from the first suture segment L by the cutting by the first cutter 51 as replacement of the other end of the first suture segment L. The other end of the second suture segment L is a newly-formed end portion that has been threaded through the needle hole (e.g., the suture hooking portion) 38 and protrudes from the second holding surface 28*b* through the needle hole 38. Thus, after suturing or knot tying is completed, a user does not need to perform preparation for the next suturing or the next knot tying, for example, manually re-setting the suture L, and thus suturing and knot tying may be performed successively.

According to the knot tying device 10 of the illustrative embodiment, the second suture hook 68 has the wire loop for holding the newly-formed end portion of the suture L passing through the needle hole 38. This enables the suture L to be caught and held by the second suture hook 68 more reliably, thereby readily preparing for the next suturing or the next tying, for example, re-setting of the suture L.

According to the knot tying device 10 of the illustrative embodiment, the loop forming portion 71 includes the suture groove, the hook groove, and the rotation shaft. The suture groove allows the suture L to extend therein. The hook groove is a groove for allowing the first suture hook 62 to pass therethrough, and extends in the direction orthogonal to the suture groove. The rotation shaft has a rotation axis extending in the direction intersecting the longitudinal direction of the first suture hook 62. In response to the loop forming portion 71 rotating about the rotation axis in a state where the suture L extends in the suture groove, a loop is formed in the suture in a state where the suture L is wound around the outer peripheral surface of the rotation shaft. Thus, the loop of the suture is formed more stably. The stable loop formation enables stable knot tying in the suture.

The knot tying device 10 according to the illustrative embodiment includes a plurality of the loop forming portions 71. Rotation axes of the plurality of loop forming portions 71 are parallel to each other. A particular loop forming portion of the plurality of loop forming portions 71 rotates in a direction opposite to a direction in which the other loop forming portions of the plurality of loop forming portions rotate. This configuration enables a knot M to be tied more firmly in the to-be-tied object 30 using the suture L for knot tying.

According to the knot tying device 10 of the illustrative embodiment, each of the loop forming portions 71 moves along the rotation axis while rotating about the rotation axis. This configuration enables the loop of the suture L to have a three-dimensional shape, thereby readily threading the suture L into the loop.

The knot tying device 10 according to the illustrative embodiment includes a plurality of the loop forming portions 71, and the suture presser 102 between the adjacent loop forming portions 71. The suture presser 102 presses the suture extending between the loop forming portions 71 at a position in the rotation axis direction before the loop forming portions 71 move toward a loop forming side in the rotation axis direction. The suture presser 102 maintains the position of the suture L in the rotation axis direction regardless of the movement of the loop forming portions 71 toward the loop forming side in the rotation axis direction. This prevents the suture L from coming out of the suture groove, thereby forming the loop of the suture L more reliably.

According to the knot tying device 10 of the illustrative embodiment, the knot tying device 10 includes the knot pusher 66. The knot pusher 66 moves the loop of the suture L formed by the loop forming portion 71 in a direction from the loop forming portion 71 toward the to-be-tied object 30. The knot pusher 66 has the guide groove 66*c* for catching and holding the suture L. Thus, the position where a knot is to be tied in the suture L may be shifted to a position adjacent to the to-be-tied object 30.

According to the knot tying device 10 of the illustrative embodiment, the suture presser 102 rotates in association with the movement of the knot pusher 66. With this configuration, the suture L held by the suture presser 102 is released, and thus the position where a knot is to be tied in the suture L may be more readily shifted to the position adjacent to the to-be-tied object 30.

According to the knot tying device 10 of the illustrative embodiment, the knot pusher 66 catches the loop and pushes the loop toward the to-be-tied object 30 in a state where the suture L extending through of the loop is tensioned. Thus, the position where a knot is to be tied in the suture L may be more readily shifted to a position adjacent to the to-be-tied object 30.

According to the knot tying device 10 of the illustrative embodiment, a plurality of loops are formed in the suture L. In response to the first suture hook 62 pulling the suture L, the loop closest to the to-be-tied object 30 among the plurality of loops moves to the position adjacent to the to-be-tied object 30, and in response to the knot pusher 66 pushing the other of the plurality of loops, the other of the plurality of loops moves to the position adjacent to the to-be-tied object 30.

According to the knot tying device 10 of the illustrative embodiment, the holding portion is the curved needle 34 that has an arc shape and penetrates the to-be-tied object 30 together with the suture L in order to suture the to-be-tied object 30. This configuration enables the knot tying device 10 to suture the to-be-tied object 30.

According to the knot tying device 10 of the illustrative embodiment, the distal end portion of the holding portion has the recess portion 40. With this configuration, interference between the holding portion and the first suture hook 62 may be avoided.

According to the knot tying device 10 of the illustrative embodiment, the knot tying device 10 includes the main body 14, the first jaw portion 12, and the second jaw portion 28. The main body 14 houses the loop forming portion 71. The first jaw portion 12 and the second jaw portion 28 each protrude from the main body 14 and have an elongated shape. The second jaw portion 28 is disposed rotatably with respect to the main body 14 and is configured to move toward and away from the first jaw portion 12. The first jaw portion 12 and the second jaw portion 28 include holding protrusions (e.g., the first holding protrusion 12a and the second holding protrusion 28a), respectively, that protrude toward each other at the respective distal end portions to hold the to-be-tied object 30. In a state where the first jaw portion 12 and the second jaw portion 28 portion are closed, the holding protrusions (e.g., the first holding protrusion 12a and the second holding protrusion 28a) of the first jaw portion 12 and the second jaw portion 28 are contactable with each other. Thus, a knot may be more reliably tied on the to-be-tied object 30 using the suture L or the to-be-tied object 30 may be more reliably sutured with the suture L.

According to the knot tying device 10 of the illustrative embodiment, the knot tying device 10 includes the main body 14 housing the loop forming portion 71. The main body 14 has a bearing hole. The loop forming portion 71 is held in the bearing hole so as to be rotatable about the rotation axis. The loop forming portion 71 includes a driving rotor, a rotary shaft, and a cam follower. The driving rotor is rotatable about the rotation axis and immovable in the rotation axis direction. The rotary shaft is engaged with the driving rotor so as not to be relatively rotatable with respect to the driving rotor but movable in the rotation axis direction. The cam follower protrudes from the rotary shaft in a radial direction of the rotary shaft and is in engagement with a spiral cam groove defined in an inner peripheral surface of the bearing hole.

According to the knot tying device 10 of the illustrative embodiment, the knot tying device 10 includes the main body 14, the first jaw portion 12, the second jaw portion 28, and the first cutter 51. The main body 14 houses the loop forming portion 71. The first jaw portion 12 and the second jaw portion 28 each protrude from the main body 14 and have an elongated shape. The second jaw portion 28 is rotatable with respect to the main body 14 and is movable toward and away from the first jaw portion 12. The first cutter 51 is disposed in the first jaw portion 12 and cuts the suture L. The holding portion is disposed in the second jaw portion 28 and is movable toward and away from the first jaw portion 12. In response to the holding portion being moved toward the first jaw portion 12 in a state where the first jaw portion 12 and the second jaw portion 28 are closed, the suture L hooked on the suture hooking portion is cut by the first cutter 51. Thus, only by operating the holding portion, a portion of the suture L unnecessary for knot tying may be cut off from the to-be-tied object 30.

According to the knot tying device 10 of the illustrative embodiment, the first cutter 51 is disposed at the position where a portion of the suture L extending after cutting has a length longer than the distance between the suture hooking portion of the holding portion and the tip of the holding portion and shorter than the distance between the first jaw portion 12 and the second jaw portion 28 that are opened relative to each other. This configuration enables the first cutter 51 to cut the suture L more reliably.

According to the knot tying device 10 of the illustrative embodiment, the knot tying device 10 includes the main body 14, the first jaw portion 12, the second jaw portion 28, and the second cutter 54. The main body 14 houses the loop forming portion 71. The first jaw portion 12 and the second jaw portion 28 each protrude from the main body 14 and have an elongated shape. The second jaw portion 28 is rotatable with respect to the main body 14 and is movable toward and away from the first jaw portion 12. The second cutter 54 is disposed in the main body 14. In response to the second jaw portion 28 opening in the direction away from the first jaw portion 12, the second cutter 54 cuts the suture L. Thus, the to-be-tied object 30 is released from the first jaw portion 12 and the second jaw portion 28, and at the same time, an excess portion of the suture L used for knot tying may be cut off from the to-be-tied object 30.

According to the knot tying device 10 of the illustrative embodiment, the first suture hook 62 may be switched between the loosely-holding state in which the suture L is allowed to slide and the securely-holding state in which the suture L is prevented from sliding. Thus, a length of the suture L required for knot tying may be freely adjusted.

According to the knot tying device 10 of the illustrative embodiment, the first suture hook 62 loosely holds the suture L in the loosely-holding state after catching the suture L until threading of the suture L through the loop is completed, and securely holds the suture L in the securely-holding state after threading of the suture L through the loop is completed. Thus, a knot may be more reliably tied in the to-be-tied object 30 using the suture L.

According to the knot tying device 10 of the illustrative embodiment, the knot tying device 10 includes the bobbin (e.g., the suture supply portion) 88. The bobbin 88 supplies the suture L to the suture hooking portion. The bobbin 88 includes the resistance member 92 that applies resistance to the suture L being supplied. This configuration thus enable knot tying on the to-be-tied object 30 and suturing of the to-be-tied object 30 to be performed successively.

The knot tying device 10 of the illustrative embodiment includes the needle 34, the loop forming portion 71, and the first suture hook 62. The needle 34 has the suture hooking portion 38 for hooking the suture L at the tip and penetrates the to-be-tied object 30. The loop forming section 71 fixedly forms a loop of the suture L. The first suture hook 62 passes through the loop formed in the suture L, and catches and holds the suture L that extends through the to-be-tied object 30 through which the needle 34 has penetrated. Then, in response to the suture L, which is held by the first suture hook 62, passing through the loop, a knot is tied in the suture L. Thus, although the suture L that has passed through the to-be-tied object 30 tends to be affected by a surface tension of body fluids, a weight of attached body fluids, or other matters, the loop forming portion 71 may form a loop in the suture L by using a portion different from the portion that has passed through the to-be-tied object 30. Thus, the stable loop formation enables stable knot tying in the suture.

The knot tying device 10 of the illustrative embodiment includes the needle 34, the loop forming portion 71, and the first suture hook 62. The needle 34 penetrates the to-be-tied object 30 with the suture L being threaded through the tip. The loop forming portion 71 includes the rotation shaft, and forms a loop of the suture L in response to rotation of the rotation shaft. The first suture hook 62 moves toward the needle 34 through the loop formed by the loop forming portion 71 and holds the suture L that has passed through the to-be-tied object 30. The first suture hook 62 passes through the loop with holding the suture L and moves back the initial position, thereby tying a knot in the suture L. Thus, although the suture L that has passed through the to-be-tied object 30 tends to be affected by a surface tension of body fluids, a weight of attached body fluids, or other matters, the loop forming portion 71 may form a loop in the suture L by using a portion different from the portion that has passed through the to-be-tied object 30. Thus, the stable loop formation enables stable knot tying in the suture.

The knot tying device 10 of the illustrative embodiment includes the holding portion for holding the suture L, the loop forming portion 71 for forming a loop in the suture L, the main body 14 for accommodating the loop forming portion 71, and the first jaw portion 12 and the second jaw portion 28 that protrude from the main body 14. The holding portion is disposed in the second jaw portion 28. The loop forming section 71 forms a loop in the suture L in the main body 14 in a state where the holding portion holds the suture L. The second jaw portion 28 is disposed at the main body 14 so as to be rotatable, and is movable toward and away from the first jaw portion 12. The second jaw portion 28 holds the to-be-tied object 30 between the first jaw portion 12 and the second jaw portion 28. Thus, a loop of the suture is stably formed without being affected by a surface tension of body fluids, a weight of attached body fluids, or other matters. The stable loop formation enables stable knot tying in the suture.

According to the knot tying device 10 of the illustrative embodiment, the loop forming portion 71 includes the first suture loop shaft 72 and the second suture loop shaft 74. The first suture loop shaft 72 rotates about the first rotation axis C1 to form a first suture loop LP1 in the suture L in the main body 14. The second suture loop shaft 74 rotates in a direction opposite to the first suture loop shaft 72 about the second rotation axis C2 parallel to the first rotation axis C1, to form a second suture loop LP2 in the suture L in the main body 14. This configuration enables a knot M to be tied more firmly in the to-be-tied object 30 using the suture L for knot tying.

According to the knot tying device 10 of the illustrative embodiment, the knot tying device 10 includes the first suture hook 62. The first suture hook 62 is movable toward the distal end of the first jaw portion 12 and the distal end of the second jaw portion 28 holding the to-be-tied object 30 therebetween by passing through the loop formed by the loop forming portion 71. The first suture hook 62 catches and holds the suture L held by the holding portion and pulls the suture L into the main body 14. Thus, a base of a knot M using the suture L is stably formed without being affected by a surface tension of body fluids, a weight of attached body fluids, or other matters.

Second Illustrative Embodiment

Next, another illustrative embodiment of the disclosure will be described. In the following description, the same reference numerals are given to common parts as those in the above-described illustrative embodiment, and the description thereof will be omitted.

Figure 46:
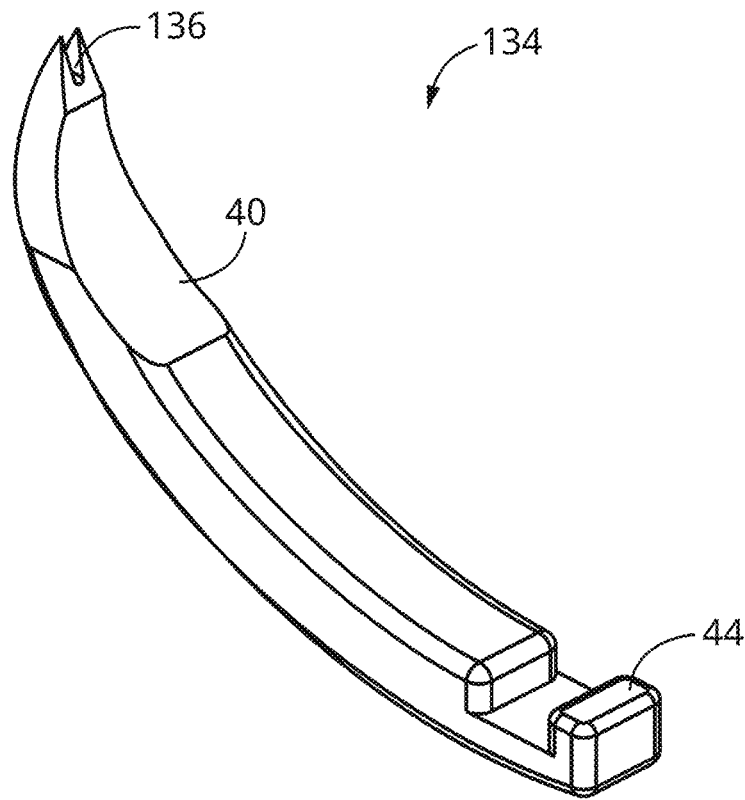
FIG. 46 is a perspective view of another example of the curved needle of FIG. 11.

FIG. 46 illustrates a curved needle 134 of another illustrative embodiment which may be used in place of the curved needle 34 of the above-described illustrative embodiment. The curved needle 134 of this illustrative embodiment has a similar configuration to the curved needle 34 of the above-described illustrative embodiment except that the curved needle hole 134 has an engagement groove 136 cut along the longitudinal direction from a needle tip instead of the needle hole 38 of the curved needle 34. The curved needle 134 of the illustrative embodiment is configured to cause the suture L hooked on the engagement groove 136 functioning as the suture hooking portion, to extend through the to-be-tied object 30 together with the needle tip of the curved needle 134, similarly to the curved needle 34 of the above-described illustrative embodiment.

Third Illustrative Embodiment

Figure 47:
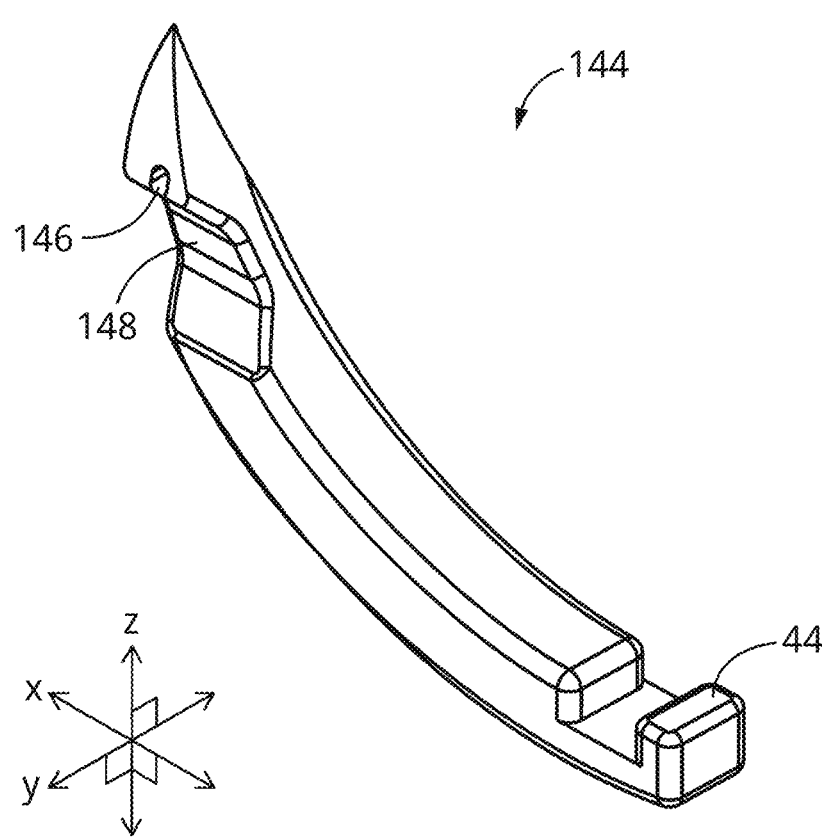
FIG. 47 is a perspective view of still another example of the curved needle of FIG. 11.

FIG. 47 illustrates a curved needle 144 of another illustrative embodiment which may be used in place of the curved needle 34 of the above-described illustrative embodiment. Instead of the needle hole 38 that is defined in the curved needle 34 of the above-described illustrative embodiment and extends through the distal end portion in the direction of a radius of curvature, the curved needle 144 of the illustrative embodiment has a needle hole 146 that extends through an distal end portion in a direction parallel to the center line of curvature of the curved needle 144 at the distal end portion. Instead of the recessed portion 40 defined on the inner peripheral surface of the distal end portion in the curved needle 34 of the above-described illustrative embodiment, the curved needle 144 has a recessed portion 148 at a side surface of a distal end portion. The curved needle 144 of the illustrative embodiment is configured to cause the suture L hooked on the needle hole 146 functioning as the suture hooking portion, to extend through the to-be-tied object 30 together with the needle tip of the curved needle 144, similarly to the curved needle 34 of the above-described illustrative embodiment. The needle housing hollow 32 illustrated in FIG. 11 of the above-described illustrative embodiment is defined in a plane including the longitudinal direction x and the height direction z, whereas a needle housing hole for housing the curved needle 144 of the illustrative embodiment is defined in a plane including the width direction y and the height direction z.

Fourth Illustrative Embodiment

Figure 48:
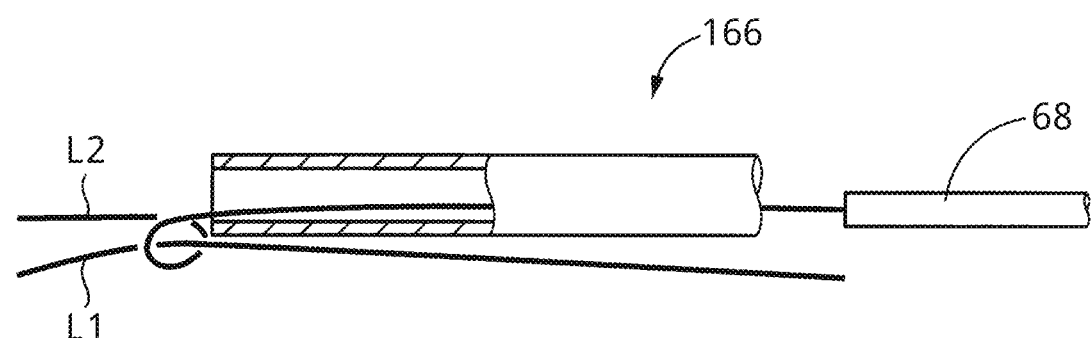
FIG. 48 illustrates another example of the knot pusher of FIG. 12.

FIG. 48 illustrates a knot pusher 166 of another illustrative embodiment which may be used in place of the knot pusher 66 of the above-described illustrative embodiment. The knot pusher 166 of the illustrative embodiment includes a tubular member that allows the second suture hook 68 holding a first portion L1 and a second portion L2 of the suture L to move therein and that is guided by the second guide hole 70 (see FIGS. 6 and 7). The knot pusher 166 of the illustrative embodiment may move the second suture loop LP2 toward the distal end of the knot tying device 10, similarly to the knot pusher 66 described above.

Although illustrative embodiments of the disclosure have been described above with reference to the drawings, the disclosure is also applied to other illustrative embodiments.

For example, a plastic wire material that may be tied is used as the suture L in the above-described illustrative embodiment. For example, a natural thread, a synthetic thread, a metallic thread, a composite thread or other appropriate threads is used as the suture L. The natural thread is a monofilament or multifilament thread made from plant or animal fibers. The synthetic thread is a monofilament or multifilament thread made of synthetic fibers. The metallic thread is a monofilament or multifilament thread made of metallic wires. The composite thread is made of natural fibers and synthetic fibers.

The knot tying device 10 of the above-described illustrative embodiment has an elongated shape having a rectangular cross section, that is, a prismatic shape, but may have a circular columnar shape having a circular cross section.

In the knot tying device 10 of the above-described illustrative embodiment, the curved needle 34 having an arc shape is used as an example of the needle, but a straight needle having a linear shape may be used.

In the knot tying device 10 of the above-described illustrative embodiment, two loops are formed in the suture L for knot tying, but three or more loops may be formed for knot tying. That is, the loop forming portion 71 of the knot tying device 10 of the above-described illustrative embodiment includes the two loop shafts, the first suture loop shaft 72 and the second suture loop shaft 74, but may include three or more suture loop shafts.

In the knot tying device 10 of the above-described illustrative embodiment, the first suture loop shaft 72 rotates counterclockwise toward the first lid member 18, and the second suture loop shaft 74 rotates clockwise toward the first lid member 18. Nevertheless, the first suture loop shaft 72 and the second suture loop shaft 74 may rotate in respective directions opposite to the directions in which the first suture loop shaft 72 and the second suture loop shaft 74 rotates in the above-described illustrative embodiment. In short, the pair of first suture loop shaft 72 and second suture loop shaft 74 may rotate in any respective directions as long as the first suture loop shaft 72 and the second suture loop shaft 74 rotate in opposite directions.

The knot tying device 10 of the above-described illustrative embodiment includes the two loop shafts, the first suture loop shaft 72 and the second suture loop shaft 74, but may include three or more suture loop shafts.

In the knot tying device 10 of the above-described illustrative embodiment, the opening/closing operation rod 60 for opening and closing the second jaw portion 28, the needle operating member 36 for causing the curved needle 34 to protrude from the second holding surface 28*b*, the catching and holding operation of the first suture hook 62, and the catching and holding operation of the second suture hook 68 may be manually operated or performed or remotely operated or performed using actuators electrically driven and controlled.

In the above-described illustrative embodiment, the needle penetrating step in which the distal end of the curved needle 34 is caused to penetrate the to-be-tied object 30 together with the suture L as illustrated in FIG. 28, the first suture hook holding step in which the first suture hook 62 moves to the vicinity of the curved needle 34 through the second suture loop LP2 and the first suture loop LP1 and catches and holds the suture L held at the distal end portion of the curved needle 34, and the first suture hook backward-moving step in which the first suture hook moves backward through the first suture loop LP1 and the second suture loop LP2 to pull out the suture L are performed in this order. Alternatively, the steps may be performed in the following order. The first suture hook 62 may be moved to the vicinity of the curved needle 34 through the second suture loop LP2 and the first suture loop LP1 after the loop forming step. Then, after the needle penetrating step, the first suture hook holding step in which the first suture hook 62 catches and holds the suture L held by the distal end portion of the curved needle 34, and the first suture hook backward-moving step in which the first suture hook 62 pulls out the suture L such that the suture L extends through the first suture loop LP1 and the second suture lope LP2 may be performed.

In the above-described illustrative embodiment, the first jaw portion 12 is fixed to the main body 14 and protrudes from the main body 14 in the longitudinal direction, but the first jaw portion 12 may be disposed so as to be rotatable with respect to the main body 14, similarly to the second jaw portion 22. In this case, the first suture hook 62 may be formed of a flexible member, and the first guide hole 64 for guiding the first suture hook 62 may be defined not only in the main body 14 but also in the first jaw portion 12, so that the first suture hook 62 can be moved to the vicinity of the curved needle 34 through the second suture loop LP2 and the first suture loop LP1.

In the above-described illustrative embodiment, the curved needle 34 that penetrates the to-be-tied object 30 is used to place sutures L in a portion of the to-be-tied object 30. Nevertheless, in a case where the to-be-tied object 30 is, for example, a blood vessel of a living body, the curved needle 34 might not necessarily be used to place sutures L in the entire to-be-tied object 30. In this case, for example, a particular portion of the second holding surface 28*b* of the second jaw portion 28 may be projected such that the particular portion has the suture groove 98 and can be engaged with the slot 50 of the first jaw portion 12. The particular portion of the second holding surface 28*b* is a portion closer to the distal end of the knot tying device 10 than the other portion and is located at a central position in the width direction y. In a state where the to-be-tied object 30 is held between the other portion and the first holding surface 12*b*, in response to the first suture hook 62 catching and holding a portion of the suture L located on a to-be-tied object 30 side of the protrusion as illustrated in FIG. 29, the suture L placed in the entire to-be-tied object 30 may be tied as illustrated in FIGS. 30 to 38.

In the loop forming portion 71 of the above-described illustrative embodiment, the cam protrusions 72*d* of the first suture loop shaft 72 are fitted to the spiral cam grooves 80*a*, respectively. This configuration enables the first suture loop shaft 72 to move along the first rotation axis C1 direction, that is, the height direction z, while rotating about the first rotation axis C1. The cam protrusions 74*d* of the second suture loop shaft 74 are fitted to the spiral cam grooves 82*a*, respectively. This configuration enables the second suture loop shaft 72 to move along the second rotation axis C2 direction, that is, the height direction z, while rotating about the second rotation axis C2. However, the first suture loop shaft 72 and the second suture loop shaft 74 might not necessarily move along the first rotation axis C1 direction and the second rotation axis C2 direction, respectively, that is, the height direction z. As illustrated in FIGS. 14 and 16, the first suture hook 62 has an obliquely cut distal end. With this configuration, in response to the first suture hook 62 being pushed toward the distal end of the knot tying device 10 while rotating, the suture L wound around the outer peripheral surfaces of the second suture loop shaft 74 and the first suture loop shaft 72 is positioned above and below the first suture hook 62, and thus, the first suture hook 62 is passed through the second suture loop LP2 and the first suture loop LP1.

While the disclosure has been described in detail with reference to the specific embodiments thereof, those are merely examples, and various changes, arrangements and modifications may be applied therein without departing from the spirit and scope of the disclosure.

What is claimed is:

1. A knot tying device, comprising:
   a holding portion including a suture hooking portion at its distal end portion, the holding portion configured to hold a suture that is engaged with the suture hooking portion;
   a first loop forming portion configured to form a loop of the suture fixedly;

a positioning portion configured to position the suture hooking portion with which the suture is engaged, at a specific position; and a first suture hook configured to:

pass through the loop; and catch and hold the suture in a state where the suture hooking portion with which the suture is engaged is located at the specific position, wherein the first suture hook causes the suture to pass through the loop, thereby tying a knot in the suture.

2. The knot tying device according to claim 1, wherein the positioning portion is configured to cause the suture hooking portion to be located at the specific position such that at least a portion of a to-be-tied object is located in a first plane space defined by of the suture extending between the suture hooking portion and a position where the loop is formed and a virtual straight line connecting between the suture hooking portion and the position where the loop is formed, wherein the first suture hook holds the suture such that the to-be-tied object is not located within a second plane space defined by virtual straight lines connecting the suture hooking portion, the position where the first suture hook is formed, and the position where the first suture hook holds the suture, and wherein a knot is tied in the suture in a state where the suture is placed around at least a portion of the to-be-tied object.

3. The knot tying device according to claim 1, further comprising:

a second suture hook configured to hold an end portion of the suture; and a first cutter configured to, after the suture hooking portion is positioned at the specific position in a state where the second suture hook holds the end portion of the suture, cut the suture into a first suture segment and a second suture segment, wherein a knot is tied in the first suture segment held by the first suture hook, and wherein after the knot is tied in the first suture segment, the second suture hook catches and holds a newly-formed end portion that is an end portion of the second suture segment as replacement of the end portion of the suture, the newly-formed end portion having been hooked on the suture hooking portion.

4. The knot tying device according to claim 1, wherein the first loop forming portion includes:

a first suture groove configured to allow the suture to extend therein;

a first hook groove configured to allow the first suture hook to move therein, the first hook groove extending in a direction orthogonal to the first suture groove; and a first rotary shaft having a first rotation axis extending in a direction intersecting a longitudinal direction of the first hook groove, wherein the first loop forming portion is configured to rotate about the first rotation axis in a state where the suture extends in the first suture groove and is wound around an outer peripheral surface of the first rotary shaft, thereby forming the loop.

5. The knot tying device according to claim 4, further comprising a second loop forming portion including a second suture groove, a second hook groove, and a second rotary shaft having a second rotation axis, wherein the first rotation axis of the first loop forming portion and the second rotation axis of the second loop forming portion extend parallel to each other, and wherein the first loop forming portion rotates in a direction opposite to a direction in which the second loop forming portion rotates.

6. The knot tying device according to claim 1, further comprising a knot pusher having a groove for catching a to-be-tied object, the knot pusher being configured to move the loop formed by the first loop forming portion toward the to-be-tied object from the first loop forming portion to shift a position where a knot is formed to a position adjacent to the to-be-tied object.

7. The knot tying device according to claim 1, wherein the holding portion includes a curved needle having an arc shape, and is configured to penetrate a to-be-tied object together with the suture in order to suture to-be-tied object.

8. The knot tying device according to claim 1, wherein the holding portion has a recessed portion at the distal end portion.

9. The knot tying device according to claim 1, further comprising:

a main body accommodating the first loop forming portion;

a first jaw portion protruding from the main body and having an elongated shape;

a second jaw portion rotatably disposed at the main body, the second jaw portion being configured to move toward and away from the first jaw portion, the second jaw portion having an elongated shape; and a holding protrusion protruding from a distal end portion of each of the first jaw portion and the second jaw portion, the holding protrusions protruding toward each other in a direction toward and away from each other, wherein the holding protrusions are in contact with each other in a state where the first jaw portion and the second jaw portion are closed.

10. The knot tying device according to claim 1, further comprising:

a main body accommodating the first loop forming portion;

a first jaw portion protruding from the main body and having an elongated shape;

a second jaw portion rotatably disposed at the main body, the second jaw portion being configured to move toward and away from the first jaw portion, the second jaw portion having an elongated shape; and a first cutter disposed in the first jaw portion, the first cutter being configured to cut the suture, wherein the holding portion is disposed in the second jaw portion so as to be movable toward and away from the first jaw portion, and wherein the first cutter cuts the suture hooked on the suture hooking portion in response to the holding portion being moved toward the first jaw portion in a state where the first jaw portion and the second jaw portion are closed.

11. The knot tying device according to claim 10, wherein the first cutter is disposed at a position where a portion of the suture extending after cutting has a length longer than a distance between a suture hooking portion of the holding portion and a tip of the holding portion and shorter than a distance between the first jaw portion and the second jaw portion that are opened relative to each other.

12. The knot tying device according to claim 1, further comprising:

a main body accommodating the first loop forming portion;

a first jaw portion protruding from the main body and having an elongated shape;

a second jaw portion rotatably disposed at the main body, the second jaw portion being configured to move toward and away from the first jaw portion, the second jaw portion having an elongated shape; and a second cutter disposed in the main body, the second cutter being configured to, in response to the second jaw portion being opened to move away from the first jaw portion, cut the suture.

13. The knot tying device according to claim 1, wherein the first suture hook is configured to be selectively in a loosely-holding state in which the suture is allowed to slide or a securely-holding state in which the suture is prevented from sliding.

14. The knot tying device according to claim 13, wherein the first suture hook loosely holds the suture in the loosely-holding state after catching the suture until threading of the suture through the loop is completed, and securely holds in the securely-holding state until the threading of the suture through the loop is completed.

15. The knot tying device according to claim 1, further comprising a suture supply portion configured to supply the suture to the suture hooking portion, the suture supply portion including a resistance member configured to apply resistance to the suture being supplied.

\* \* \* \* \*